US011154586B2

United States Patent
Knight

(10) Patent No.: US 11,154,586 B2
(45) Date of Patent: *Oct. 26, 2021

(54) TREATING SEXUAL DYSFUNCTION

(71) Applicant: Olive Therapeutics, LLC, Belmont, MA (US)

(72) Inventor: E. Quattrocki Knight, Belmont, MA (US)

(73) Assignee: Olive Therapeutics, LLC, Belmont, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/876,554

(22) Filed: May 18, 2020

(65) Prior Publication Data

US 2020/0384065 A1    Dec. 10, 2020

Related U.S. Application Data

(63) Continuation of application No. 16/345,170, filed as application No. PCT/US2017/058533 on Oct. 26, 2017, now Pat. No. 10,709,756.

(60) Provisional application No. 62/413,328, filed on Oct. 26, 2016.

(51) Int. Cl.
*A61K 38/095* (2019.01)
*A61P 15/00* (2006.01)
*A61K 9/00* (2006.01)
*A61K 31/137* (2006.01)

(52) U.S. Cl.
CPC .......... *A61K 38/095* (2019.01); *A61K 9/0043* (2013.01); *A61K 31/137* (2013.01); *A61P 15/00* (2018.01)

(58) Field of Classification Search
CPC .. A61K 38/095; A61K 9/0043; A61K 31/137; A61P 15/00
See application file for complete search history.

(56) References Cited

U.S. PATENT DOCUMENTS

| | | |
|---|---|---|
| 4,640,921 A | 2/1987 | Othmer et al. |
| 6,448,276 B1 | 9/2002 | Yerxa |
| 6,462,047 B1 | 10/2002 | Bombrun et al. |
| 10,709,756 B2 | 7/2020 | Knight |
| 2002/0143188 A1 | 10/2002 | Garvey et al. |
| 2002/0150625 A1 | 10/2002 | Kryger |
| 2002/0187165 A1 | 12/2002 | Harbeck |

(Continued)

FOREIGN PATENT DOCUMENTS

| | | |
|---|---|---|
| DE | 4321965 A1 | 1/1995 |
| EP | 1468690 A1 | 10/2004 |

(Continued)

OTHER PUBLICATIONS

Alper, K. et al, Seizure incidence in psychopharmacological clinical trials: an analysis of Food and Drug Administration (FDA) summary basis of approval reports, Biol. Psychiatry, 62:345-354 (2007).

(Continued)

*Primary Examiner* — Trevor Love
(74) *Attorney, Agent, or Firm* — Choate, Hall & Stewart LLP; Brenda Herschbach Jarrell; John P. Rearick

(57) ABSTRACT

The present disclosure describes use of oxytocin, in combination with one or more other agents as described herein, for use for example in the treatment of certain conditions.

25 Claims, 4 Drawing Sheets

(56) References Cited

U.S. PATENT DOCUMENTS

| | | |
|---|---|---|
| 2003/0195186 A1 | 10/2003 | Shapira |
| 2004/0077540 A1* | 4/2004 | Quay .................. A61K 9/0043 424/94.64 |
| 2008/0003275 A1 | 1/2008 | Vaisman |
| 2008/0269233 A1 | 10/2008 | Andrews et al. |
| 2011/0021564 A1* | 1/2011 | Sanfilippo ............... A61P 25/30 514/317 |
| 2014/0045804 A1 | 2/2014 | Lichten |
| 2016/0271102 A1 | 9/2016 | Epstein |
| 2018/0193340 A1 | 7/2018 | Knight |
| 2018/0250300 A1 | 9/2018 | Knight |
| 2019/0282653 A1 | 9/2019 | Knight |
| 2021/0137923 A1 | 5/2021 | Knight |

FOREIGN PATENT DOCUMENTS

| | | |
|---|---|---|
| WO | WO-2004/067022 A2 | 8/2004 |
| WO | WO-2010/057117 A2 | 5/2010 |
| WO | WO-2016/201286 A1 | 12/2016 |
| WO | WO-2018/081427 A1 | 5/2018 |
| WO | WO-2018/129461 A1 | 7/2018 |

OTHER PUBLICATIONS

Anderson-Hunt, M. and Dennerstein, L., Increased female sexual response after oxytocin, BMJ, 309(6959):929 (1994).
Argiolas, A. and Melis, M.R., Neuropeptides and central control of sexual behaviour from the past to the present: a review, Prog. Neurobiol., 108:80-107 (2013).
Argiolas, A. and Melis, M.R., The role of oxytocin and the paraventricular nucleus in the sexual behaviour of male mammals, Physiol. Behav., 83(2):309-317 (2004).
Bales, K.L. and Carter, C.S., Developmental exposure to oxytocin facilitates partner preferences in male prairie voles (Microtus ochrogaster), Behav. Neurosci., 117(4): 854-859 (2003).
Balon, R., Bupropion and nightmares, Am J Psychiatry, 153:579-580 (1996).
Bartz, J.D., et al., Oxytocin can hinder trust and cooperation in borderline personality disorder, Social Cognitive and Affective Neuroscience, 6(5): 556-563 (2011).
Baskerville, T.A., and Douglas, A.J., Interactions between dopamine and oxytocin in the control of sexual behaviour, Prog. Brain Res., 170:277-290 (2008).
Baumgartner, T.M., et al., Oxytocin shapes the neural circuitry of trust and trust adaptation in humans, Neuron, 58:639-650 (2008).
Behnia, B., et al., Differential effects of intranasal oxytocin on sexual experiences and partner interactions in couples, Horm. Behav., 65(3):308-318 (2014).
Boyd, N.R., Oxytocin in human parturition, Proc. R. Soc. Med, 65(5):491-492 (1972).
Brown, C.H. et al., Physiological regulation of magnocellular neurosecretory cell activity: integration of intrinsic, local and afferent mechanisms, J. Neuroendocrinol, 25(8):678-710 (2013).
Burri, A. et al., The acute effects of intranasal oxytocin administration on endocrine and sexual function in males, Psychoneuroendocrinology, 33(5): 591-600 (2008).
Cara, A.M. et al., The role of histamine in human penile erection, Br. J. Urol., 75(2):220-224 (1995).
Carmichael, M.S. et al., Relationships among cardiovascular, muscular, and oxytocin responses during human sexual activity, Arch. Sex Behav., 23(1):59-79 (1994).
Carmichael, M.S., et al., Plasma oxytocin increases in the human sexual response, J. Clin. Endocrinol. Metab., 64(1): 27-31 (1987).
Carro-Juarez, M. and Rodriguez-Manzo, G., Evidence for the presence and functioning of the spinal generator for ejaculation in the neonatal male rat, International journal of impotence research, 17:270-276 (2005).
Carro-Juarez, M. and Rodriguez-Manzo, G., The spinal pattern generator for Ejaculation, Brain Res Rev, 58:106-120 (2008).
Carro-Juarez, M. et al, Pro-ejaculatory effect of the aqueous crude extract of cihuapatli (Montanoa tomentosa) in spinal male rats, J. Ethnopharmacol., 106:111-116 (2006).
Carro-Juarez, M., and Rodriguez-Manzo, G., Evidence for the presence of the spinal pattern generator involved in the control of the genital ejaculatory pattern in the female rat, Brain research, 1084:54-60 (2006).
Carro-Juárez, M. et al, Evidence for the involvement of a spinal pattern generator in the control of the genital motor pattern of ejaculation, Brain research, 975:222-228 (2003).
Clayton A. et al, Burden of phase-specific sexual dysfunction with SSRIs, Journal of affective disorders, 91:27-32 (2006).
De Dreu, C.K., et al., Oxytocin Motivates Non-Cooperation in Intergroup Conflict to Protect Vulnerable In-Group Members, PLoS One, 7(11):e46751 (2012).
De Jong, T.R. and Neumann, I.D., Moderate Role of Oxytocin in the Pro-Ejaculatory Effect of the 5-HTIA Receptor Agonist 8-OH-DPAT, J. Sex Med., 12(1):17-28 (2015).
Dinsmore, W.W., and Wyllie, M.G., Vasoactive intestinal polypeptide/phentolamine for intracavemosal injection in erectile dysfunction, BJU Int., 102(8):933-937 (2008).
Dong, Y. Y., et al, K2P channel gating mechanisms revealed by structures of TREK-2 and a complex with Prozac, Science, 347(6227): 1256-1259 (2015).
Feifel, D. and Reza, T., Oxytocin modulates psychotomimetic-induced deficits in sensorimotor gating, Psychopharmacology, 141:93-98 (1999).
Feifel, D. et al., Adjunctive intranasal oxytocin reduces symptoms in schizophrenia patients, Biol. Psychiatry, 68:678-680 (2010).
Feifel, D. et al., The effects of oxytocin and its analog, carbetocin, on genetic deficits in sensorimotor gating, Eur. Neuropsychopharmacol., 22(5):374-378 (2012).
Feifel, D., et al., Adjunctive intranasal oxytocin improves verbal memory in people with schizophrenia, Schizophr. Res., 139(1-3):207-210 (2012).
Feifel, David, Oxytocin as a potential therapeutic target for schizophrenia and other neuropsychiatric conditions, Neuropsychopharmacology, 37(1):304-305 (2012).
Fuchs, A.R. and Fuchs, F., Endocrinology of human parturition: a review, Br. J. Obstet. Gynaecol., 91(10): 948-967 (1984).
Giraldi, A. et al., Oxytocin and the initiation of parturition. A review, Dan Med Bull, 37(4):377-383 (1990).
Gollasch, M. et al, Perivascular adipose tissue and the dynamic regulation of $K_v7$ and $K_{ir}$ channels: Implications for resistant hypertension, Microcirulation., 24: e12434 (2018).
Grillner, S. and Wallen, P., Central pattern generators for locomotion, with special reference to vertebrates, Annual review of neuroscience, 8:233-261 (1985).
Grillner, S. et al, Microcircuits in action—from CPGs to neocortex, Trends in neurosciences, 28: 525-533 (2005).
Haeger, K. and Jacobsohn, D., A contribution to the study of milk ejection in women, Acta. Physiol. Scand. Suppl., 111:152-160 (1953).
Hatton, G.I., and Wang, Y.F., Neural mechanisms underlying the milk ejection burst and reflex, Prog. Brain Res., 170:155-166 (2008).
Heil, S.H. and Subramanian, M.G., Alcohol and the hormonal control of lactation, Alcohol Health Res World, 22(3):178-184 (1998).
Igarashi, H. et al, Development of Simplified Vasoactive Intestinal Peptide Analogs with Receptor Selectivity and Stability for Human Vasoactive Intestinal Peptide/Pituitary Adenylate Cyclase-Activating Polypeptide Receptors, Journal of Pharmacology and Experimental Therapeutics, 315(1):370 (2005).
Insel, T.R. et al., Molecular aspects of monogamy, Ann NY Acad. Sci., 807:302-316 (1997).
Insel, T.R. et al., Oxytocin and the molecular basis of monogamy, Adv. Exp. Med. Biol., 395:227-234 (1995).
Insel, T.R., and Shapro, L.E., Oxytocin receptors and maternal behavior, Ann. NY Acad. Sci., 652:122-141 (1992).
Insel, T.R., Regional changes in brain oxytocin receptors postpartum: time-course and relationship to maternal behaviour, J. Neuroendocrinol., 2(4):539-545 (1990).

(56) References Cited

OTHER PUBLICATIONS

International Search Report for PCT/US2017/058533 (Treating Sexual Dysfunction, filed Oct. 26, 2017), issued by ISA/US, 3 pages (dated Jan. 9, 2018).
International Search Report for PCT/US2018/012805 (Treatment of Sexual Dysfunction, filed Jan. 8, 2018), issued by ISA/US, 3 pages (dated Feb. 28, 2018).
Ishak, W. et al., Male anorgasmia treated with oxytocin, J. Sex Med, 5(4):1022-1024 (2008).
Israel, J.M. et al, Neonatal testosterone suppresses a neuroendocrine pulse generator required for reproduction, Nature communications, 5:3285 (2014).
Jing, J. et al., From Hunger to Satiety: Reconfiguration of a Feeding Network by Aplysia Neuropeptide Y., The Journal of Neuroscience, 27(13):3490-3502 (2007).
Kennedy, S.H. and Rizvi, S., Sexual dysfunction, depression, and the impact of Antidepressants, Journal of clinical psychopharmacology, 29:157-164 (2009).
Kennett, J.E. and McKee, D.T., Oxytocin: an emerging regulator of prolactin secretion in the female rat, J. Neuroendocrinol., 24(3):403-412 (2012).
Keri, S. and Kiss, I., Oxytocin response in a trust game and habituation of arousal, Physiol. Behav., 102(2):221-224 (2011).
Kirkwood, P.A., and Ford, T.W., Do respiratory neurons control female receptive behavior: a suggested role for a medullary central pattern generator?, Progress in brain research, 143:105-114 (2004).
Kosfeld, M. et al., Oxytocin increases trust in humans, Nature, 435:673-676 (2005).
Kruger, T. et al., Serial neurochemical measurement of cerebrospinal fluid during the human sexual response cycle, Eur. J. Neurosci., 24(12):3445-3452 (2006).
Kruger, T. et al., Specificity of the neuroendocrine response to orgasm during sexual arousal in men, J. Endocrinol., 177(1):57-64 (2003).
Labbate, L.A. et al, Serotonin reuptake antidepressant effects on sexual function in patients with anxiety disorders, Biol. Psychiatry, 43:904-907 (1998).
Landen, M. et al, Effect of buspirone on sexual dysfunction in depressed patients treated with selective serotonin reuptake inhibitors, Journal of Clinical Psychopharmacol., 19(3): 268-71 (1999). [Abstract].
Lange, A.B., Neural mechanisms coordinating the female reproductive system in the locust, Frontiers in bioscience (Landmark edition), 14:4401-4415 (2009).
Lazzari, V. et al., Oxytocin modulates social interaction but is not essential for sexual behavior in male mice, Behav. Brain Res., 244:130-136 (2013).
Leininger, E.C., and Kelley, D.B., Evolution of Courtship Songs in Xenopus: Vocal Pattern Generation and Sound Production, Cytogenetic and genome Research, 145:302-314 (2015).
Levin, R. J. and Wagner, G. , Human vaginal fluid-ionic composition and modification by sexual arousal [proceedings], J. Physiol., 266(1): 62P-63P (1977).
Levin, R. J., The pharmacology of the human female orgasm—Its biological and physiological backgrounds, 11, Pharmacology Biochemistry and Behavior, 121:62-70 (2014).
Lidberg, L. and Sternthal, V., A new approach to the hormonal treatment of impotentia erectionis, Pharmakopsychiatr Neuropsychopharmakol, 10(1):21-25 (1977).
Long, C.-Y. et al, A randomized comparative study of the effects of oral and topical estrogen therapy on the vaginal vascularization and sexual function in hysterectomized postmenopausal women, Menopause, 13(5): 737-743 (2006). [Abstract and full article].
Lytton, J. et al, K+-dependent Na+/Ca2+ exchangers in the brain, Ann. NY Acad. Sci., 976: 382-393 (2002).
MacDonald, K. and Feifel, D., Dramatic improvement in sexual function induced by intranasal oxytocin, J Sex Med, 9(5):1407-1410 (2012).
MacDonald, K. and Feifel, D., Helping oxytocin deliver: considerations in the development of oxytocin-based therapeutics for brain disorders, Front Neurosci., 7:35 (2013).
MacDonald, K. and Feifel, D., Oxytocin in schizophrenia: a review of evidence for its therapeutic effects, Acta. Neuropsychiatr., 24(3):130-146 (2012).
MacDonald, K. and MacDonald, T., The peptide that binds: a systematic review of oxytocin and its prosocial effects in humans, Harv. Rev. Psychiatry, 18(1):1-21 (2010).
MacDonald, K., Patient-clinician eye contact: social neuroscience and art of clinical engagement, Postgrad Med, 121(4):136-144 (2009).
MacDonald, K.S., Sex, receptors, and attachment: a review of individual factors influencing response to oxytocin, Front Neurosci., 6:194 (2012).
Martin L.A., et al, The experience of symptoms of depression in men vs women: analysis of the National Comorbidity Survey Replication, JAMA Psychiatry, 70:1100-1106 (2013).
McCarthy, M. et al., An anxiolytic action of oxytocin is enhanced by estrogen in the mouse, Physiol. Behav., 60:1209-1215 (1996).
Messenger, A.G. and Rundegren, J., Minoxidil: mechanisms of action on hair growth, British Journal of Dermatology, 150: 186-194 (2004).
Meston, C. and Heiman, J. R., Ephedrine-Activated Physiological Sexual Arousal in Women, Arch. Gen. Psychiatry, 55: 652-656 (1998).
Monteiro W.O., Anorgasmia from clomipramine in obsessive-compulsive disorder. A controlled trial, Br. J. Psychiatry, 151:107-112(1987).
Montejo A.L. et al, Sexual side-effects of antidepressant and antipsychotic drugs, Current opinion in psychiatry, 28:418-423 (2015). [Abstract Only].
Montgomery, S. et al., Antidepressant medications: a review of the evidence for drug-induced sexual dysfunction, Journal of Affective Disorders, 69(1-3):119-140 (2002).
Muin, D.A. et al, Effect of long-term intranasal oxytocin on sexual dysfunction in premenopausal and postmenopausal women: a randomized trial, Fertility and Sterility, 104(3): 715-23 (2015).
Murphy, M. et al., Changes in oxytocin and vasopressin secretion during sexual activity in men, J. Clin. Endocrinol. Metab., 65(4):738-741 (1987).
Nelson, E., Sex and antidepressants: When to switch drugs or try an antidote, Current Psychiatry, 3(11): 53-66 (2004).
Nishimori, K. et al., Oxytocin is required for nursing but is not essential for parturition or reproductive behavior, Proc. Natl. Acad. Sci. USA, 93(21):11699-11704 (1996).
Nurnberg, H.G. An evidence-based review updating the various treatment and management approaches to serotonin reuptake inhibitor-associated sexual dysfunction, Drugs of today (Barcelona, Spain:1998), 44:147-168 (2008).
Ogawa, S. et al., Increase in oxytocin secretion at ejaculation in male, Clin. Endocrinol. (Oxf), 13(1):95-97(1980).
Pfaus, J. et al., Bremelanotide: an overview of preclinical CNS effects on female sexual function, J Sex Med, 4 Suppl. 4:269-279 (2007).
Quattrocki, E. A. et al, A Shab potassium channel contributes to action potential broadening in peptidergic neurons, Neuron, 12(1): 73-86 (1994).
Reiter, R.J. et al, Melatonin and reproduction revisited, Biology of reproduction, 81:445-456 (2009).
Renfrew, J. et al., Oxytocin for promoting successful lactation, Cochrane Database Syst. Rev(2): CD000156 (2000). [Abstract Only].
Rooij, K. V. et al., Pharmacokinetics of a Prototype Formulation of Sublingual Testosterone and a Buspirone Tablet, Versus an Advanced Combination Tablet of Testosterone and Buspirone in Healthy Premenopausal Women, Drugs in Rand D, 14(2):125-132 (2014).
Salmina, A. et al., CD38/cyclic ADP-ribose system: a new player for oxytocin secretion and regulation of social behaviour, J. Neuroendocrinol., 22(5):380-392 (2010).
Scheele, D. et al., An oxytocin-induced facilitation of neural and emotional responses to social touch correlates inversely with autism traits, Neuropsychopharmacology, 39(9):2078-2085 (2014).

(56) References Cited

OTHER PUBLICATIONS

Segraves R.T. and Balon, R., Antidepressant-induced sexual dysfunction in men, Pharmacology Biochemistry and Behavior, 121:132-137 (2014).

Serretti A., and Chiesa, A., Sexual side effects of pharmacological treatment of psychiatric diseases, Clin. Pharmacol. Ther., 89:142-147 (2011).

Shapiro, L. and Insel, T., Oxytocin receptor distribution reflects social organization in monogamous and polygamous voles, Ann. NY Acad. Sci., 652:448-451 (1992).

Sheng, F. et al., Oxytocin modulates the racial bias in neural responses to others' suffering, Biol. Psychol., 92(2):380-386 (2013).

Surkan P.J. et al, Preventing infant and child morbidity and mortality due to maternal depression, Best Pract. Res. Clin. Obstet. Gynaecol., 36:156-168 (2016).

Taylor, M.J., et al, Strategies for managing sexual dysfunction induced by antidepressant medication, The Cochrane database of systematic reviews, Cd003382, 136 pages (2013).

Tribolet, E. et al., Gonadal steroids regulate oxytocin receptors but not vasopressin receptors in the brain of male and female rats, An autoradiographical study, Brain Research 511(1):129-140 (1990).

Von Philipsborn, A.C. et al, Neuronal control of *Drosophila* courtship song, Neuron, 69:509-522 (2011).

Walch, K. et al., The effect of single-dose oxytocin application on time to ejaculation and seminal parameters in men, J. Assist Reprod. Genet, 18(12):655-659 (2001).

Wang, T., The Effects of the Potassium Channel Opener Minoxidil on Renal Electrolytes Transport in the Loop of Henle, Journal of Pharmacology and Experimental Therapeutics, 304(2): 833-840 (2003).

Weiss, K.R. et al, Peptidergic co-transmission in Aplysia: functional implications for rhythmic behaviors, Experientia, 48:456-463 (1992).

Williams, J. et al., Oxytocin administered centrally facilitates formation of a partner preference in female prairie voles (*Microtus ochrogaster*), J. Neuroendocrinol., 6(3):247-250 (1994).

Written Opinion for PCT/US2017/058533 (Treating Sexual Dysfunction, filed Oct. 26, 2017), issued by ISA/US, 4 pages (dated Jan. 9, 2018).

Written Opinion for PCT/US2018/012805 (Treatment of Sexual Dysfunction, filed Jan. 8, 2018), issued by ISA/US, 10 pages (dated Feb. 28, 2018).

Yamamoto, D., and Koganezawa, M. Genes and circuits of courtship behaviour in *Drosophila* males, Nature reviews Neuroscience, 14: 681-692 (2013).

Young, L. et al., Anatomy and neurochemistry of the pair bond, J. Comp. Neurol., 493(1):51-57 (2005).

Young, L. et al., Neuroendocrine bases of monogamy, Trends Neurosci., 21(2):71-75 (1998).

Croft, H. A., Understanding the Role of Serotonin in Female Hypoactive Sexual Desire Disorder and Treatment Options, The Journal of Sexual Medicine, 14:1575-1584 (2017).

Michelson, D. et al., Female Sexual Dysfunction Associated With Antidepressant Administration: A Randomized, Placebo-Controlled Study of Pharmacologic Intervention, Am J Psychiatry, 157:2 (2000).

\* cited by examiner

TREATING SEXUAL DYSFUNCTION

CROSS REFERENCE TO RELATED APPLICATIONS

The present application is a continuation of U.S. application Ser. No. 16/345,170, now U.S. Pat. No. 10,709,756, which issued on Jul. 14, 2020, which is a National Stage Entry of Patent Cooperation Treaty application number PCT/US2017/058533, filed on Oct. 26, 2017, which claims priority to U.S. Provisional patent application No. 62/413,328, filed on Oct. 26, 2016, the entire disclosure of each of which is incorporated herein by reference.

BACKGROUND

Sexual dysfunction can affect both men and women, with significant negative impact(s) on their quality of life and enjoyment.

SUMMARY

The present disclosure provides an insight that combination of oxytocin with certain other therapeutic agents may be particularly effective for the treatment of sexual dysfunction.

BRIEF DESCRIPTION OF THE DRAWING

FIG. 1 presents a schematic representing two different modes of interaction between the parasympathetic and sympathetic arms of the autonomic nervous system. The loop to the left of the middle arrow depicts homeostatic conditions. The circular arrows pointing in the counterclockwise direction symbolizes the regulatory, balancing interaction between the two arms of the autonomic nervous system. Under normal conditions, the parasympathetic and sympathetic systems counteract each other, maintaining the organism's homeostatic set point. The balancing/regulatory mode of interaction between the sympathetic and parasympathetic arms is well accepted and considered general knowledge. The depiction to the right of the middle arrow represents a new conceptualization related to the proposed disclosure. The loop to the right of central arrow describes the proposed interaction between the two arms of the autonomic nervous system during successful sexual function. Unlike the counterbalancing feedback necessary for regulating homeostasis, this disclosure proposes that the sympathetic and parasympathetic systems reinforce each other during sexual function.

DEFINITIONS

Figure 1:
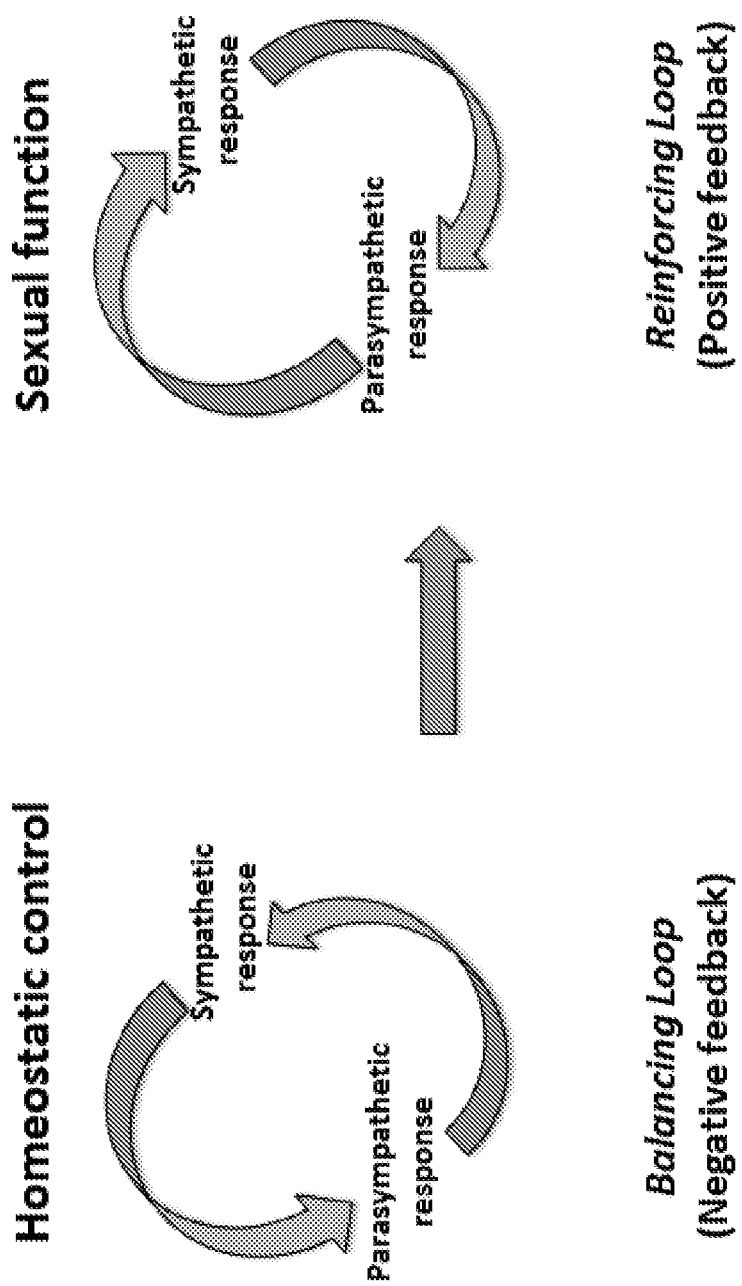
FIG. 1. This disclosure proposes that the feedback within the autonomic nervous system undergoes a transition during sexual activity. This

Activating agent: As used herein, the term "activating agent" refers to an entity, condition, or event whose presence, level, or degree correlates with elevated level or activity of a target, as compared with that observed absent the agent (or with the agent at a different level). In some embodiments, an activating agent may act directly (in which case it exerts its influence directly upon its target, for example by binding to the target); in some embodiments, an activating agent may act indirectly (in which case it exerts its influence by interacting with and/or otherwise altering a regulator of the target, so that level and/or activity of the target is increased). In some embodiments, an activating agent is one whose presence or level correlates with a target level or activity that is comparable to or greater than a particular reference level or activity (e.g., that observed under appropriate reference conditions, such as presence of a known activating agent, e.g., a positive control).

Administration: As used herein, the term "administration" typically refers to the administration of a composition to a subject or system. Those of ordinary skill in the art will be aware of a variety of routes that may, in appropriate circumstances, be utilized for administration to a subject, for example a human. For example, in some embodiments, administration may be ocular, oral, parenteral, topical, etc. In some particular embodiments, administration may be bronchial (e.g., by bronchial instillation), buccal, dermal (which may be or comprise, for example, one or more of topical to the dermis, intradermal, interdermal, transdermal, etc), enteral, intra-arterial, intradermal, intragastric, intramedullary, intramuscular, intranasal, intraperitoneal, intrathecal, intravenous, intraventricular, within a specific organ (e. g. intrahepatic), mucosal, nasal, oral, rectal, subcutaneous, sublingual, topical, tracheal (e.g., by intratracheal instillation), vaginal, vitreal, etc. In some embodiments, administration may involve dosing that is intermittent (e.g., a plurality of doses separated in time) and/or periodic (e.g., individual doses separated by a common period of time) dosing. In some embodiments, administration may involve continuous dosing (e.g., perfusion) for at least a selected period of time.

Agent: In general, the term "agent", as used herein, may be used to refer to a compound or entity of any chemical class including, for example, a polypeptide, nucleic acid, saccharide, lipid, small molecule, metal, or combination or complex thereof. In appropriate circumstances, as will be clear from context to those skilled in the art, the term may be utilized to refer to an entity that is or comprises a cell or organism, or a fraction, extract, or component thereof. Alternatively or additionally, as context will make clear, the term may be used to refer to a natural product in that it is found in and/or is obtained from nature. In some instances, again as will be clear from context, the term may be used to refer to one or more entities that is man-made in that it is designed, engineered, and/or produced through action of the hand of man and/or is not found in nature. In some embodiments, an agent may be utilized in isolated or pure form; in some embodiments, an agent may be utilized in crude form. In some embodiments, potential agents may be provided as collections or libraries, for example that may be screened to identify or characterize active agents within them. In some cases, the term "agent" may refer to a compound or entity that is or comprises a polymer; in some cases, the term may refer to a compound or entity that comprises one or more polymeric moieties. In some embodiments, the term "agent" may refer to a compound or entity that is not a polymer and/or is substantially free of any polymer and/or of one or more particular polymeric moieties. In some embodiments, the term may refer to a compound or entity that lacks or is substantially free of any polymeric moiety.

Analog: As used herein, the term "analog" refers to a substance that shares one or more particular structural features, elements, components, or moieties with a reference substance. Typically, an "analog" shows significant structural similarity with the reference substance, for example sharing a core or consensus structure, but also differs in certain discrete ways. In some embodiments, an analog is a substance that can be generated from the reference substance, e.g., by chemical manipulation of the reference substance. In some embodiments, an analog is a substance that can be generated through performance of a synthetic process substantially similar to (e.g., sharing a plurality of steps with) one that generates the reference substance. In some embodiments, an analog is or can be generated through performance of a synthetic process different from that used to generate the reference substance.

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (for example when the one or more values of interest define a sufficiently narrow range that application of such a percentage variance would obviate the stated range).

Associated with: Two events or entities are "associated" with one another, as that term is used herein, if the presence, level and/or form of one is correlated with that of the other. For example, a particular entity (e.g., polypeptide, genetic signature, metabolite, microbe, etc) is considered to be associated with a particular disease, disorder, or condition, if its presence, level and/or form correlates with incidence of and/or susceptibility to the disease, disorder, or condition (e.g., across a relevant population). In some embodiments, two or more entities are physically "associated" with one another if they interact, directly or indirectly, so that they are and/or remain in physical proximity with one another. In some embodiments, two or more entities that are physically associated with one another are covalently linked to one another; in some embodiments, two or more entities that are physically associated with one another are not covalently linked to one another but are non-covalently associated, for example by means of hydrogen bonds, van der Waals interaction, hydrophobic interactions, magnetism, and combinations thereof.

Biologically active: as used herein, refers to an observable biological effect or result achieved by an agent or entity of interest. For example, in some embodiments, a specific binding interaction is a biological activity. In some embodiments, modulation (e.g., induction, enhancement, or inhibition) of a biological pathway or event is a biological activity. In some embodiments, presence or extent of a biological activity is assessed through detection of a direct or indirect product produced by a biological pathway or event of interest.

Biological Sample: As used herein, the term "biological sample" typically refers to a sample obtained or derived from a biological source (e.g., a tissue or organism or cell culture) of interest, as described herein. In some embodiments, a source of interest comprises an organism, such as an animal or human. In some embodiments, a biological sample is or comprises biological tissue or fluid. In some embodiments, a biological sample may be or comprise bone marrow; blood; blood cells; ascites; tissue or fine needle biopsy samples; cell-containing body fluids; free floating nucleic acids; sputum; saliva; urine; cerebrospinal fluid, peritoneal fluid; pleural fluid; feces; lymph; gynecological fluids; skin swabs; vaginal swabs; oral swabs; nasal swabs; washings or lavages such as a ductal lavages or broncheoalveolar lavages; aspirates; scrapings; bone marrow specimens; tissue biopsy specimens; surgical specimens; feces, other body fluids, secretions, and/or excretions; and/or cells therefrom, etc. In some embodiments, a biological sample is or comprises cells obtained from an individual. In some embodiments, obtained cells are or include cells from an individual from whom the sample is obtained. In some embodiments, a sample is a "primary sample" obtained directly from a source of interest by any appropriate means. For example, in some embodiments, a primary biological sample is obtained by methods selected from the group consisting of biopsy (e.g., fine needle aspiration or tissue biopsy), surgery, collection of body fluid (e.g., blood, lymph, feces etc.), etc. In some embodiments, as will be clear from context, the term "sample" refers to a preparation that is obtained by processing (e.g., by removing one or more components of and/or by adding one or more agents to) a primary sample. For example, filtering using a semi-permeable membrane. Such a "processed sample" may comprise, for example nucleic acids or proteins extracted from a sample or obtained by subjecting a primary sample to techniques such as amplification or reverse transcription of mRNA, isolation and/or purification of certain components, etc.

Biomarker: The term "biomarker" is used herein, consistent with its use in the art, to refer to a to an entity whose presence, level, or form, correlates with a particular biological event or state of interest, so that it is considered to be a "marker" of that event or state. To give but a few examples, in some embodiments, a biomarker may be or comprise a marker for a particular disease state, or for likelihood that a particular disease, disorder or condition may develop, occur, or reoccur. In some embodiments, a biomarker may be or comprise a marker for a particular disease or therapeutic outcome, or likelihood thereof. Thus, in some embodiments, a biomarker is predictive, in some embodiments, a biomarker is prognostic, in some embodiments, a biomarker is diagnostic, of the relevant biological event or state of interest. A biomarker may be an entity of any chemical class. For example, in some embodiments, a biomarker may be or comprise a nucleic acid, a polypeptide, a lipid, a carbohydrate, a small molecule, an inorganic agent (e.g., a metal or ion), or a combination thereof. In some embodiments, a biomarker is a cell surface marker. In some embodiments, a biomarker is intracellular. In some embodiments, a biomarker is found outside of cells (e.g., is secreted or is otherwise generated or present outside of cells, e.g., in a body fluid such as blood, urine, tears, saliva, cerebrospinal fluid, etc.

Combination therapy: As used herein, the term "combination therapy" refers to those situations in which a subject is simultaneously exposed to two or more therapeutic regimens (e.g., two or more therapeutic agents). In some embodiments, the two or more regimens may be administered simultaneously; in some embodiments, such regimens may be administered sequentially (e.g., all "doses" of a first regimen are administered prior to administration of any doses of a second regimen); in some embodiments, such agents are administered in overlapping dosing regimens. In some embodiments, "administration" of combination therapy may involve administration of one or more agent(s) or modality(ies) to a subject receiving the other agent(s) or modality(ies) in the combination. For clarity, combination therapy does not require that individual agents be administered together in a single composition (or even necessarily at the same time), although in some embodiments, two or more agents, or active moieties thereof, may be administered together in a combination composition, or even in a combination compound (e.g., as part of a single chemical complex or covalent entity).

Comparable: As used herein, the term "comparable" refers to two or more agents, entities, situations, sets of conditions, etc., that may not be identical to one another but that are sufficiently similar to permit comparison there between so that one skilled in the art will appreciate that conclusions may reasonably be drawn based on differences or similarities observed. In some embodiments, comparable sets of conditions, circumstances, individuals, or populations are characterized by a plurality of substantially identical features and one or a small number of varied features. Those of ordinary skill in the art will understand, in context, what degree of identity is required in any given circumstance for two or more such agents, entities, situations, sets of conditions, etc. to be considered comparable. For example, those of ordinary skill in the art will appreciate that sets of circumstances, individuals, or populations are comparable to one another when characterized by a sufficient number and type of substantially identical features to warrant a reasonable conclusion that differences in results obtained or phenomena observed under or with different sets of circumstances, individuals, or populations are caused by or indicative of the variation in those features that are varied.

Corresponding to: As used herein, the term "corresponding to" may be used to designate the position/identity of a structural element in a compound or composition through comparison with an appropriate reference compound or composition. For example, in some embodiments, a monomeric residue in a polymer (e.g., an amino acid residue in a polypeptide or a nucleic acid residue in a polynucleotide) may be identified as "corresponding to" a residue in an appropriate reference polymer. For example, those of ordinary skill will appreciate that, for purposes of simplicity, residues in a polypeptide are often designated using a canonical numbering system based on a reference related polypeptide, so that an amino acid "corresponding to" a residue at position 190, for example, need not actually be the $190^{th}$ amino acid in a particular amino acid chain but rather corresponds to the residue found at 190 in the reference polypeptide; those of ordinary skill in the art readily appreciate how to identify "corresponding" amino acids.

Designed: As used herein, the term "designed" refers to an agent (i) whose structure is or was selected by the hand of man; (ii) that is produced by a process requiring the hand of man; and/or (iii) that is distinct from natural substances and other known agents.

Dosage form or unit dosage form: Those skilled in the art will appreciate that the term "dosage form" may be used to refer to a physically discrete unit of an active agent (e.g., a therapeutic or diagnostic agent) for administration to a subject. Typically, each such unit contains a predetermined quantity of active agent. In some embodiments, such quantity is a unit dosage amount (or a whole fraction thereof) appropriate for administration in accordance with a dosing regimen that has been determined to correlate with a desired or beneficial outcome when administered to a relevant population (i.e., with a therapeutic dosing regimen). Those of ordinary skill in the art appreciate that the total amount of a therapeutic composition or agent administered to a particular subject is determined by one or more attending physicians and may involve administration of multiple dosage forms.

Dosing regimen: Those skilled in the art will appreciate that the term "dosing regimen" may be used to refer to a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which is separated in time from other doses. In some embodiments, individual doses are separated from one another by a time period of the same length; in some embodiments, a dosing regimen comprises a plurality of doses and at least two different time periods separating individual doses. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen comprises a first dose in a first dose amount, followed by one or more additional doses in a second dose amount same as the first dose amount. In some embodiments, a dosing regimen is correlated with a desired or beneficial outcome when administered across a relevant population (i.e., is a therapeutic dosing regimen).

"Improve," "increase," or "reduce": As used herein or grammatical equivalents thereof, indicate values that are relative to a baseline or other reference measurement, such as a measurement in a particular system (e.g., in a single individual) otherwise comparable conditions absent presence of (e.g., prior to and/or after) a particular agent or treatment, or a measurement in comparable system known or expected to respond in a particular way, in presence of the relevant agent or treatment.

Inhibitory agent: As used herein, the term "inhibitory agent" refers to an entity, condition, or event whose presence, level, or degree correlates with decreased level or activity of a target). In some embodiments, an inhibitory agent may act directly (in which case it exerts its influence directly upon its target, for example by binding to the target); in some embodiments, an inhibitory agent may act indirectly (in which case it exerts its influence by interacting with and/or otherwise altering a regulator of the target, so that level and/or activity of the target is reduced). In some embodiments, an inhibitory agent is one whose presence or level correlates with a target level or activity that is reduced relative to a particular reference level or activity (e.g., that observed under appropriate reference conditions, such as presence of a known inhibitory agent, or absence of the inhibitory agent in question, etc).

Pharmaceutical composition: As used herein, the term "pharmaceutical composition" refers to a composition in which an active agent is formulated together with one or more pharmaceutically acceptable carriers. In some embodiments, the active agent is present in unit dose amount appropriate for administration in a therapeutic regimen that shows a statistically significant probability of achieving a predetermined therapeutic effect when administered to a relevant population. In some embodiments, a pharmaceutical composition may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces.

Pharmaceutically acceptable: As used herein, the term "pharmaceutically acceptable" applied to the carrier, diluent, or excipient used to formulate a composition as disclosed herein means that the carrier, diluent, or excipient must be compatible with the other ingredients of the composition and not deleterious to the recipient thereof.

Prevent or prevention: as used herein when used in connection with the occurrence of a disease, disorder, and/or condition, refers to reducing the risk of developing the disease, disorder, and/or condition and/or to delaying onset of one or more characteristics or symptoms of the disease, disorder, or condition. Prevention may be considered complete when onset of a disease, disorder, or condition has been delayed for a predefined period of time.

Reference: As used herein describes a standard or control relative to which a comparison is performed. For example, in some embodiments, an agent, animal, individual, population, sample, sequence or value of interest is compared with a reference or control agent, animal, individual, population, sample, sequence or value. In some embodiments, a reference or control is tested and/or determined substantially simultaneously with the testing or determination of interest. In some embodiments, a reference or control is a historical reference or control, optionally embodied in a tangible medium. Typically, as would be understood by those skilled in the art, a reference or control is determined or characterized under comparable conditions or circumstances to those under assessment. Those skilled in the art will appreciate when sufficient similarities are present to justify reliance on and/or comparison to a particular possible reference or control.

Solid form: As is known in the art, many chemical entities (in particular many organic molecules and/or many small molecules) can adopt a variety of different solid forms such as, for example, amorphous forms and/or crystalline forms (e.g., polymorphs, hydrates, solvates, etc). In some embodiments, such entities may be utilized as a single such form (e.g., as a pure preparation of a single polymorph). In some embodiments, such entities may be utilized as a mixture of such forms.

Subject: As used herein "subject" means an organism, typically a mammal (e.g., a human, in some embodiments including prenatal human forms). In some embodiments, a subject is suffering from a relevant disease, disorder, or condition. In some embodiments, a subject is susceptible to a disease, disorder, or condition. In some embodiments, a subject displays one or more symptoms or characteristics of a disease, disorder, or condition. In some embodiments, a subject does not display any symptom or characteristic of a disease, disorder, or condition. In some embodiments, a subject is someone with one or more features characteristic of susceptibility to or risk of a disease, disorder, or condition. In some embodiments, a subject is a patient. In some embodiments, a subject is an individual to whom diagnosis and/or therapy is and/or has been administered.

Susceptible to: An individual who is "susceptible to" a disease, disorder, or condition is at risk for developing the disease, disorder, or condition. In some embodiments, an individual who is susceptible to a disease, disorder, or condition does not display any symptoms of the disease, disorder, or condition. In some embodiments, an individual who is susceptible to a disease, disorder, or condition has not been diagnosed with the disease, disorder, and/or condition. In some embodiments, an individual who is susceptible to a disease, disorder, or condition is an individual who has been exposed to conditions associated with development of the disease, disorder, or condition. In some embodiments, a risk of developing a disease, disorder, and/or condition is a population-based risk (e.g., family members of individuals suffering from the disease, disorder, or condition).

Therapeutically Effective Amount: As used herein, the term "therapeutically effective amount" means an amount that is sufficient, when administered to a population suffering from or susceptible to a disease, disorder, and/or condition in accordance with a therapeutic dosing regimen, to treat the disease, disorder, and/or condition. In some embodiments, a therapeutically effective amount is one that reduces the incidence and/or severity of, stabilizes one or more characteristics of, and/or delays onset of, one or more symptoms of the disease, disorder, and/or condition. Those of ordinary skill in the art will appreciate that the term "therapeutically effective amount" does not in fact require successful treatment be achieved in a particular individual. Rather, a therapeutically effective amount may be that amount that provides a particular desired pharmacological response in a significant number of subjects when administered to patients in need of such treatment. For example, in some embodiments, term "therapeutically effective amount", refers to an amount which, when administered to an individual in need thereof in the context of inventive therapy, will block, stabilize, attenuate, or reverse a cancer-supportive process occurring in said individual, or will enhance or increase a cancer-suppressive process in said individual. In the context of cancer treatment, a "therapeutically effective amount" is an amount which, when administered to an individual diagnosed with a cancer, will prevent, stabilize, inhibit, or reduce the further development of cancer in the individual. A particularly preferred "therapeutically effective amount" of a composition described herein reverses (in a therapeutic treatment) the development of a malignancy such as a pancreatic carcinoma or helps achieve or prolong remission of a malignancy. A therapeutically effective amount administered to an individual to treat a cancer in that individual may be the same or different from a therapeutically effective amount administered to promote remission or inhibit metastasis. As with most cancer therapies, the therapeutic methods described herein are not to be interpreted as, restricted to, or otherwise limited to a "cure" for cancer; rather the methods of treatment are directed to the use of the described compositions to "treat" a cancer, i.e., to effect a desirable or beneficial change in the health of an individual who has cancer. Such benefits are recognized by skilled healthcare providers in the field of oncology and include, but are not limited to, a stabilization of patient condition, a decrease in tumor size (tumor regression), an improvement in vital functions (e.g., improved function of cancerous tissues or organs), a decrease or inhibition of further metastasis, a decrease in opportunistic infections, an increased survivability, a decrease in pain, improved motor function, improved cognitive function, improved feeling of energy (vitality, decreased malaise), improved feeling of well-being, restoration of normal appetite, restoration of healthy weight gain, and combinations thereof. In addition, regression of a particular tumor in an individual (e.g., as the result of treatments described herein) may also be assessed by taking samples of cancer cells from the site of a tumor such as a pancreatic adenocarcinoma (e.g., over the course of treatment) and testing the cancer cells for the level of metabolic and signaling markers to monitor the status of the cancer cells to verify at the molecular level the regression of the cancer cells to a less malignant phenotype. For example, tumor regression induced by employing the methods of this invention would be indicated by finding a decrease in any of the pro-angiogenic markers discussed above, an increase in anti-angiogenic markers described herein, the normalization (i.e., alteration toward a state found in normal individuals not suffering from cancer) of metabolic pathways, intercellular signaling pathways, or intracellular signaling pathways that exhibit abnormal activity in individuals diagnosed with cancer. Those of ordinary skill in the art will appreciate that, in some embodiments, a therapeutically effective amount may be formulated and/or administered in a single dose. In some embodiments, a therapeutically effective amount may be formulated and/or administered in a plurality of doses, for example, as part of a dosing regimen.

Treatment: As used herein, the term "treatment" (also "treat" or "treating") refers to any administration of a therapy that partially or completely alleviates, ameliorates, relives, inhibits, delays onset of, reduces severity of, and/or reduces incidence of one or more symptoms, features, and/or causes of a particular disease, disorder, and/or condition. In some embodiments, such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition.

Unit dose: The expression "unit dose" as used herein refers to an amount administered as a single dose and/or in a physically discrete unit of a pharmaceutical composition. In many embodiments, a unit dose contains a predetermined quantity of an active agent. In some embodiments, a unit dose contains an entire single dose of the agent. In some embodiments, more than one unit dose is administered to achieve a total single dose. In some embodiments, administration of multiple unit doses is required, or expected to be required, in order to achieve an intended effect. A unit dose may be, for example, a volume of liquid (e.g., an acceptable carrier) containing a predetermined quantity of one or more therapeutic agents, a predetermined amount of one or more therapeutic agents in solid form, a sustained release formulation or drug delivery device containing a predetermined amount of one or more therapeutic agents, etc. It will be appreciated that a unit dose may be present in a formulation that includes any of a variety of components in addition to the therapeutic agent(s). For example, acceptable carriers (e.g., pharmaceutically acceptable carriers), diluents, stabilizers, buffers, preservatives, etc., may be included as described infra. It will be appreciated by those skilled in the art, in many embodiments, a total appropriate daily dosage of a particular therapeutic agent may comprise a portion, or a plurality, of unit doses, and may be decided, for example, by the attending physician within the scope of sound medical judgment. In some embodiments, the specific effective dose level for any particular subject or organism may depend upon a variety of factors including the disorder being treated and the severity of the disorder; activity of specific active compound employed; specific composition employed; age, body weight, general health, sex and diet of the subject; time of administration, and rate of excretion of the specific active compound employed; duration of the treatment; drugs and/or additional therapies used in combination or coincidental with specific compound(s) employed, and like factors well known in the medical arts.

DETAILED DESCRIPTION OF CERTAIN EMBODIMENTS

Sexual Dysfunction

For purposes of present disclosure, sexual dysfunction includes, for example, impairment in sexual desire, arousal, orgasm, or satisfaction, any or all of which may be due to, for example, psychogenic, biologic (including, but not limited to: vasogenic, endocrine related, menopause, and neurologic disorders), or medication-induced mechanisms. Sexual dysfunction, as used herein, does not include premature ejaculation, sexual pain, or sexual paraphilias.

Sexual dysfunction can sometimes arise after treatment with particular therapeutic agents. For example, sexual dysfunction is a known side effect of therapy with certain selective serotonin re-uptake inhibitors, certain combinations of selective norepinephrine and serotonin re-uptake inhibitors, certain anti-hypertensive medications (e.g., alpha-2 adreno-receptor antagonists, beta-blockers, etc), certain antipsychotics (e.g., D2 antagonists), etc.

Current medication strategies for treatment of sexual dysfunction in women are designed to target known underlying medical causes, such as thyroid hormone for hypothyroidism and hormone replacement for menopause. The only currently approved medication for premenopausal women without a clear underlying medical cause, Flibanserin (trade name Addyi®), is designed to increase the frequency of satisfying sexual encounters. The exact mechanism of the drug is incompletely understood, but is believed to involve increases in norepinephrine and dopamine levels, coupled with a simultaneous decrease in serotonin release. Flibanserin is reported to act as an agonist to the serotonin 1A (5HT-1A) receptor, as a weak antagonist to the 5-HT2A receptor, and may show weak partial antagonism to the dopamine D4 receptor. The FDA recently approved this treatment (specifically, 100 mg pill taken orally at bedtime) for female hypoactive sexual interest/arousal dysfunction (FSIAD), but modest efficacy, the requirement to abstain from alcohol and the necessity of daily dosing, regardless of sexual frequency, have prevented this medication from becoming widely used. Furthermore, black box contraindications including (in addition to alcohol use), liver impairment, and concurrent use with other hepatic enzyme CYP3/4A inhibitors, combined with a risk of syncope and some concern about increased breast cancer risk have further discouraged its adoption. Moreover, flibanserin is only indicated for premenopausal women, despite the high prevalence of hypoactive sexual desire disorder in post menopausal women.

In males, current therapies have more successfully mitigated sexual dysfunction, but have primarily been designed to enhance erections, not facilitate orgasm. The typical approach inhibits the phosphodiesterase enzyme (PDE5) from degrading cyclic guanosine monophosphate (cGMP) after nitric oxide has bound with soluble guanylate cyclase. The cGMP causes vasodilation (by relaxing smooth muscle) of the corpus cavernosum capillary bed, leading to subsequent tissue engorgement (erection). Typical drugs in this class include sildenafil (Viagra®), tadalafil (Cialis®), and vardenafil (Levitra®). Certain PDE5 inhibitor agents are marketed for oral administration (specifically, Viagra®, Levitra®, Cialis®, are typically prescribed in 25-100 mg doses taken by mouth approximately 4 hours to 30 minutes prior to engagement, as needed, but no more than once per day); alternatively or additionally, certain PDE5 inhibitor agents are marketed for sublingual and/or buccal administration. Clinical trials by Pfizer indicate that 63-82% of men with erectile dysfunction experience improved erectile dysfunction on Viagra®).

Other treatments for male erectile dysfunction also attempt to promote tissue engorgement through smooth muscle relaxation and subsequent vasodilation, but are either less effective than the phosphodiesterase inhibitors or require direct injection into the corpus cavernosum at the base of the penis. For example, Trimix® (a combination of phentolamine, PGE1, papivarine, administered in 0.025-0.5 microgram doses), histamine (administered in 30-60 microgram doses (Cara, Lopes-Martins et al. 1995)), and Invicorp® (a combination of 25 micrograms of Vasoactive Intestinal Peptide (VIP), an alpha-adrenergic antagonist that occludes venal outflow from the corpus cavernosum of the penis, with 1-2 mg of phentolamine mesylate, an alpha-adrenergic antagonist that increases blood flow thereto so that the combination allows for tissue engorgement (Dinsmore and Wyllie 2008)).

Vasodilators (Prostaglandins, alpha-adrenergic blockers, histamine) and antispasmodic drugs (opium alkaloids) have been used alone and in combination to treat men with some success.

However, hypotension and headache are fairly common side effects of many of these modalities. Post marketing reports of vision problems have been distributed by the FDA. Men (and women) currently using nitrates for cardiac issues, men (and women) with cardiac output deficiencies, orthostatic hypotension, or hypovolemia should not take PDE5 inhibitors.

Combination Therapy

As indicated above, the present disclosure provides the insight that combination therapy with oxytocin and one or more certain other therapeutic agents, e.g., as described herein, can be particularly useful and/or effective in the treatment of sexual dysfunction.

Provided technologies for treating sexual dysfunction as described herein, may be particularly useful or effective in patient populations such as, but not restricted to:

1. individuals with delayed orgasm or difficulty achieving orgasm secondary to psychotropic medications such as the SSRI's.
2. Post menopausal woman (the only current treatment available for woman, Flibanserin, is restricted to premenopausal women).
3. Individuals who do not adequately respond to available medications or are unable to tolerate available medications because of side effects or contraindications.
4. Males with hypoactive sexual desire.

Dosing: In contrast to flibanserin dosing, which requires patients to take the medication on a daily basis regardless of whether they anticipate imminent sexual behavior, the combination treatment provided by the present disclosure could be administered on an as needed basis, from approximately 30 minutes to six hours prior to anticipated engagement.

Oxytocin

Oxytocin is a phylogenetically ancient nonapeptide, highly conserved in the animal kingdom, that transduces many functions of the autonomic nervous system, particularly those subserving successful reproduction. Oxytocin acts as a hormone in the body, where it promotes lactation (Haeger and Jacobsohn 1953, Heil and Subramanian 1998, Renfrew, Lang et al. 2000, Hatton and Wang 2008) and facilitates parturition (Boyd 1972, Fuchs and Fuchs 1984, Giraldi, Enevoldsen et al. 1990); yet, also functions in the brain, where it participates in sculpting social behavior. Oxytocin can promote pair bonding (Shapiro and Insel 1992, Williams, Insel et al. 1994, Insel, Winslow et al. 1995, Insel, Young et al. 1997, Young, Wang et al. 1998, Bales and Carter 2003, Young, Murphy Young et al. 2005), initiate maternal care-giving (Insel 1990, Insel and Shapiro 1992), and encourage community oriented actions (Kosfeld, Heinrichs et al. 2005, Baumgartner, Heinrichs et al. 2008, Keri and Kiss 2011), all effects that support survival and reproduction.

Oxytocin is currently available as prescription therapeutic, compounded and/or marketed for use in a variety of different formats and/or for various indications. For example, Oxytocin is currently marketed in both brand name (Pitocin, Syntocini) and generic injectable preparations for use in stimulating uterine contractions, e.g., to facilitate childbirth and/or to minimize postpartum hemorrhage.

Oxytocin is also available in some European countries (Syntocinon®) and compounded in pharmacies in the United States as an intranasal form (typically 10 International Units/mL). It is believed to facilitate nursing by causing muscles around milk glands to squeeze milk into ducts. It is also sometimes prescribed for treatment of autism, sexual arousal, delayed orgasm in men and/or postorgasmic penile detumescence.

A topical gel formulation of oxytocin is available, recommended for use in facilitating both male and female orgasm. A sublingual oxytocin formulation has also been reported.

Combination therapy regimens currently recommended for oxytocin include combination with prostaglandins for labor induction, and combination with dopamine antagonists for treatment of autism (see, for example, Baskervill and Douglas, 2010).

The present disclosure encompasses the recognition that oxytocin may be useful and/or effective in certain other therapeutic contexts, specifically including sexual dysfunction, and particularly when combined with one or more particular other agents, as described herein. In preferred embodiments, oxytocin is administered intranasally, orally, sublingually, or topically.

As a nonapeptide involved in the behaviors and biology underpinning successful reproduction, oxytocin participates to some degree in several aspects of sexual functioning. Various reports indicate that oxytocin can augment sexual behavior in male rats, for review see (Argiolas and Melis 2013); yet, other studies have cast doubt on the significance of oxytocin's role (Nishimori, Young et al. 1996, Lazzari, Becker et al. 2013, de Jong and Neumann 2015). Fewer human studies exist. One study in 1974 demonstrated that oxytocin levels increased in response to nipple and genitalia stimulation in humans (Lidberg and Sternthal 1977) (Lidberg, 1974). Several small studies have shown an increase in oxytocin levels during arousal and orgasm compared to baseline in humans (Ogawa, Kudo et al. 1980, Carmichael, Humbert et al. 1987, Carmichael, Warburton et al. 1994); whereas, another report catalogued an increase in plasma oxytocin levels at the time of orgasm, but not during the arousal phase in 10 men (Murphy, Seckl et al. 1987). More recent studies have found only inconsistent and non-statistically significant changes in plasma oxytocin levels (Kruger, Haake et al. 2003) and cerebrospinal fluid concentrations of oxytocin (Kruger, Schiffer et al. 2006) during the sexual response in males. Despite a possible correlation between oxytocin levels and the sexual response, only three studies have explored administration of oxytocin on sexual functioning in humans. These studies conclude that exogenous oxytocin does not alter biological measures of sexual functioning in either men (Walch, Eder et al. 2001, Burri, Heinrichs et al. 2008) or in couples (Behnia, Heinrichs et al. 2014) when administered intra-nasally. Thus, several reports suggest that oxytocin contributes to human sexual behavior, although the significance of its role remains unknown.

Due to the inconsistent findings in the studies attempting to correlate changes of oxytocin levels during the sexual response and the lack of significant enhancement of biological measures of sexual functioning with exogenous administration of oxytocin described above, the therapeutic use of oxytocin for the treatment of sexual dysfunction has not been extensively explored. The present disclosure, however, provides insights that might explain oxytocin's observed inconsistent effects on sexual functioning, when given as a single medication, in the clinical investigations described to date (Walch, Eder et al. 2001, Burri, Heinrichs et al. 2008, Behnia, Heinrichs et al. 2014). The first reason relates to the opposing actions of the parasympathetic and sympathetic nervous systems and the other explanation rests on the context sensitivity of this neuropeptide.

As noted above, no obvious or consistent effect on sexual function has been observed during the extensive use of exogenous oxytocin since the 1960's to augment uterine contractions during labor and delivery and to facilitate the letdown reflex during breast feeding, except for one case report published in 1994 described below (Anderson-Hunt and Dennerstein 1994). Nor has any sexual benefit been described during the use of oxytocin while exploring its pro-social effect on behavior. Three case reports, described below, have been published describing a beneficial effect of oxytocin on sexual functioning; the present disclosure appreciates that information in these reports may indicate that oxytocin could have previously unrecognized and useful value once the particular situations that allowed for oxytocin's enhancement are appreciated.

Case 1: The first case report was published in 1994 in the British Medical Journal and described a 26 year old woman who experienced increased sexual desire, stronger uterine contractions during orgasm, and greater satisfaction 2 hours after self-administration of intra-nasal oxytocin ("OT") (16 IU) for treatment of breast feeding difficulties (Anderson-Hunt and Dennerstein 1994). This effect was repeated a second time 2 days later, but a third administration of OT 2 weeks later did not produce the same sexual enhancement. Besides occurring at a different time point in her menstrual cycle, contraceptive methods differed between the two time points. The patient had been on a progesterone only pill during the cycle where OT had a positive effect, but had switched to a barrier method 2 weeks prior to the third OT dose. The authors of this report acknowledge that differences in the hormonal milieu, due to alterations in the patient's menstrual cycle, may have affected the prosexual effects of OT. They did not focus on the direct effect of exogenous progesterone and its possible role in augmenting the beneficial effect of oxytocin nor did they suggest combining progesterone with OT as a possible future treatment for female sexual dysfunction. That this was published almost 20 years ago and yet OT in combination with progesterone has never been pursued as a treatment for female sexual dysfunction suggests that this possibility has not been considered as a potential application.

Case 2: The second case report, published more recently by the Journal of Sexual Medicine in 2012, describes sexual enhancement in a 32 year old married man who took intranasal oxytocin off-label for social anxiety symptoms (MacDonald and Feifel 2012). The authors report broad spectrum enhancement of the patient's sexual function concurrent with the use of the intranasal oxytocin: including, increased libido, more rapid arousal, stronger erection, and more intense and satisfying orgasm. The patient's medical history included a comorbid diagnosis of attention deficit hyperactivity disorder, (ADHD). His ADHD symptoms responded well to lisdexamfetamine treatment prior to the initiation of intranasal oxytocin. Although the authors do not specifically state that the patient continued taking this medication during the oxytocin trial, his improvement on the lisdexamfetamine and the absence of mentioning a need to terminate this medication, suggests that the patient continued the lisdexamfetamine throughout treatment with oxytocin. At no point in the report do the authors mention the possibility of an interaction between the lisdexamfetamine and the oxytocin.

The authors of this second case report study the effect of oxytocin on the sexual response, social behavior, and brain disorders, and have published several articles in this field (Feifel and Reza 1999, MacDonald 2009, Feifel, Macdonald et al. 2010, Macdonald and Macdonald 2010, Feifel 2012, Feifel, Macdonald et al. 2012, Feifel, Shilling et al. 2012, Macdonald and Feifel 2012 (Acta Neuropsychiatr), MacDonald and Feifel 2012 (J Sex Med), Macdonald 2012, Macdonald and Feifel 2013). There is no evidence that they recognized or considered any possible interaction between oxytocin and the amphetamine. The present disclosure therefore identifies the source of a problem in this work in that the researchers apparently did not appreciate that the effects on sexual function/performance they had begun to observe through oxytocin might have been enhanced by combined exposure of the subject to oxytocin and amphetamine, as may have occurred, at least to some degree, during treatment of the patient. The present disclosure provides the missing insight and, moreover, provides a variety of combination therapy regimens, as described herein.

Case 3: The third case report describes the off-label use of intranasal oxytocin to treat a four year history of anorgasmia in an 82 year-old married male (Ishak, Berman et al. 2008). The patient also experienced a history of erectile dysfunction mitigated by the use of a penile prosthesis. The man had co-morbid diabetes mellitus and coronary artery disease, but no documented psychiatric illness. Prior to the use of intranasal oxytocin, the patient had been treated with a dopamine agonist and growth hormone. The patient experienced transient but not sustained benefits with these interventions. The subsequent use of oxytocin elicited sustained restoration of his ability to achieve orgasm, but the authors did not report any improvement of his erectile dysfunction.

The present disclosure provides the insight that the preceding treatment of the patient in Case 3 with both a dopamine agonist and growth hormone may have altered the physiological environment that subsequently allowed oxytocin to have its beneficial effect. Unfortunately, the sparse documentation provided by the report does not allow for reasonable inferences to be made.

The present disclosure proposes the possibility that prior use of growth hormone by the patient in Case 3 might have impacted his subsequent benefit from oxytocin, noting that, in rats, a growth hormone analogue can facilitate the release of oxytocin (Argiolas and Melis 2004).

This present disclosure also observes that no follow-up has been reported with respect to Case 3, for example exploring whether some men who experience anorgasmia might benefit from intranasal oxytocin as a single agent.

The present disclosure further provides the insight that, in the two case reports describing use of oxytocin to treat sexual dysfunction in males (case 2 and case 3), the beneficial effects of oxytocin appear to result from subtle changes in context that the authors either did not specifically identify and/or did not appreciate. The present disclosure therefore identifies the source of a problem in the analyses provided by these case reports with respect to desirable therapeutic uses of and/or regimens for oxytocin.

Among other things, the present disclosure observes that, in case 2, the patient appeared to be concomitantly taking a long acting dopaminergic agonist (Lisdexamphetamine). This pharmacologic agent could have augmented the beneficial effects of oxytocin, given that dopaminergic pathways may interact with the oxytocin system in the paraventricular nucleus of the hypothalamus (Baskerville and Douglas 2008). The authors of the report make no mention of this possible interaction. The present disclosure also observes that, in case 3, the patient had experienced both a dopaminergic drug trial as well as a trial of growth hormone. Both of these therapies might have altered the pharmacological context, but the dosages, timing, and duration of these interventions were not specifically noted. In the single case report of the sexually enhancing effects of oxytocin in a woman, the progesterone supplementation during the first two doses may have synergistically enhanced oxytocin's effect to provide pro-sexual benefits. The authors acknowledged that changes in the hormonal milieu may have altered oxytocin's effect, but attributed this to endogenous changes in the woman's menstrual cycle.

Thus, the present disclosure provides an insight that these prior reports apparently failed to appreciate impact of the context of oxytocin administration; the present disclosure, recognizing this failure, then evidences that new therapeutic regimens, that achieve substantially simultaneous exposure of patients to both oxytocin and another agent as described herein, are useful and effective, for example in treatment of sexual dysfunction. That those skilled in the art, as the authors of these reports were, could have come so close to claimed methods without discovering them highlights the non-obviousness of combining oxytocin with another agent to enable a synergistic effect on sexual functioning.

Oxytocin Enhancing Agents

The present disclosure appreciates that few functions in the body require the concomitant activation of both the parasympathetic and sympathetic autonomic nervous systems. Typically, these two autonomic systems act in an opposing fashion. The sympathetic nervous system stimulates the "fight or flight" response; whereas, the parasympathetic nervous system oversees the neuro-vegetative functions termed "rest and digest" or "feed and breed." The human sexual response typically falls under the domain of the parasympathetic system, given the above dichotomies. Parasympathetic mechanisms dictate many aspects of sexuality, including penile erection and vaginal lubrication; yet, the final stage of the human sexual response, orgasm, requires activation of the sympathetic nervous system. This final stage of the sexual response has not been extensively studied, yet a failure to achieve orgasm commonly occurs in women and as a side effect of many psychotropic medications, including the popular serotonin reuptake inhibitors, for review see Montgomery et al, 2002 (Montgomery, Baldwin et al. 2002).

Medications that affect the autonomic nervous system typically target either the sympathetic or the parasympathetic nervous systems, not both. Because the two arms of the autonomic nervous system in most physiological conditions oppose one another (please see FIG. 1, left panel), no current medications directly activate both the sympathetic and parasympathetic arms simultaneously. Although oxytocin, an endogenous neuropeptide, appears to transduce primarily parasympathetic objectives, it also can interact with sympathetic neurotransmitter systems. Neuropeptides often do not have a straightforward effect on just one neurotransmitter system, but instead, interact with several systems to produce a coordinated action (Jing, Vilim et al. 2007). The present disclosure provides technologies for improving functioning by uniquely combining oxytocin with medications that can augment its effect. Among other things, the present disclosure teaches that oxytocin's unique role as a coordinator of other neurotransmitter systems will allow such a combination to efficaciously stimulate both arms of the autonomic nervous system without provoking the typical opposing actions that combinations of traditional parasympathetic and sympathetic medications would incite.

Figure 2:
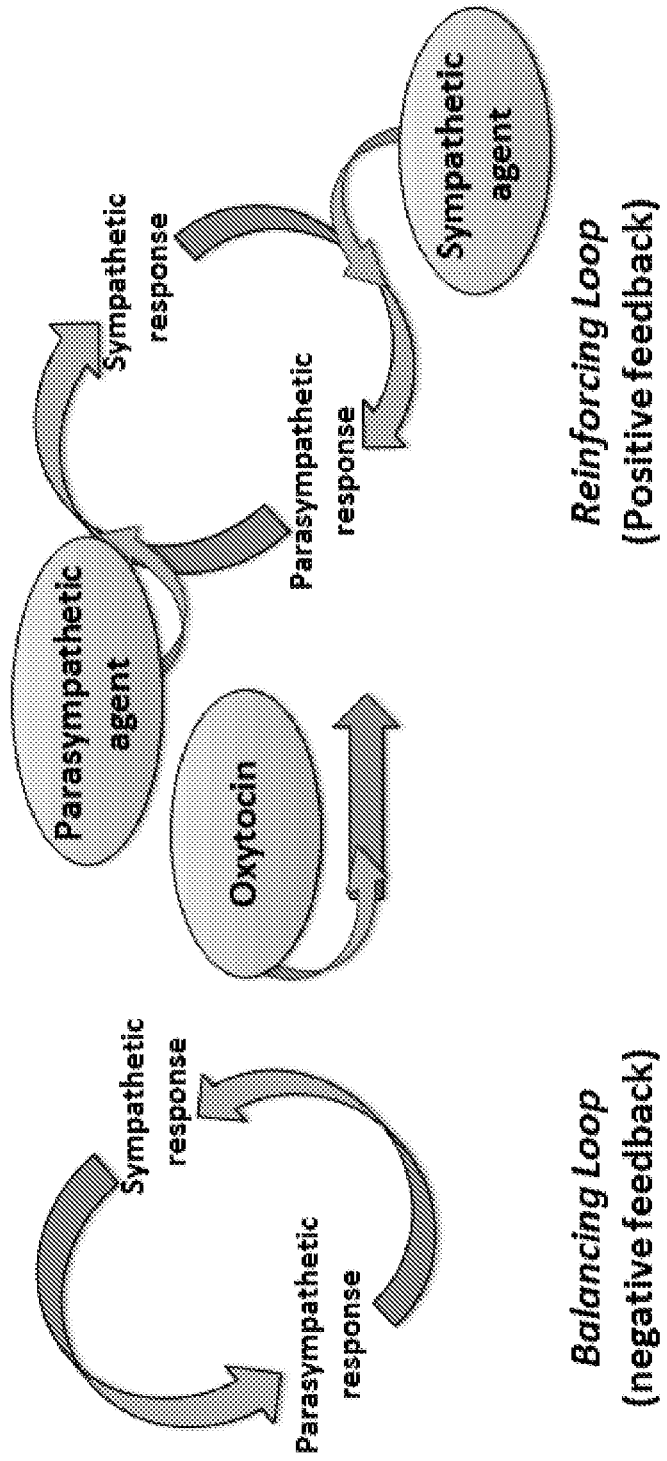
FIG. 2 presents a proposed model for interaction of sympathetic and parasympathetic systems in accordance with the present disclosure. In this proposed model A, oxytocin acts as the unknown variable and participates in transforming the mode of interaction between the sympathetic and parasympathetic arms of the autonomic nervous system from balancing to reinforcing. As the orchestrator of this transition, oxytocin modulates the biological context allowing other agents (that target either the parasympathetic or sympathetic systems) to help drive and thereby enhance the sexual response. Oxytocin itself, in addition to promoting the switch from a balancing loop to a reinforcing loop, could also help drive the sexual response as an augmenting parasympathetic agent. As in FIG. 1, in this FIG. 2, the loop to the left of the middle arrow depicts homeostatic conditions. The circular arrows pointing in the counterclockwise direction denote the regulatory, balancing interaction between the two arms of the autonomic nervous system. The loop to the right of central arrow, with the circular arrows pointing in the clockwise direction, symbolize the reinforcing interaction that oxytocin has helped promote. The oxytocin-mediated transition would then allow the addition of parasympathetic and/or sympathetic enhancing agents, that would normally counteract each other, to enter into the reinforcing cycle of positive feedback, facilitating the sexual response. In this model, oxytocin could both provide the context for other agents to enhance the sexual response and contribute as a driving agent by participating as a parasympathetic agent.
Figure 3:
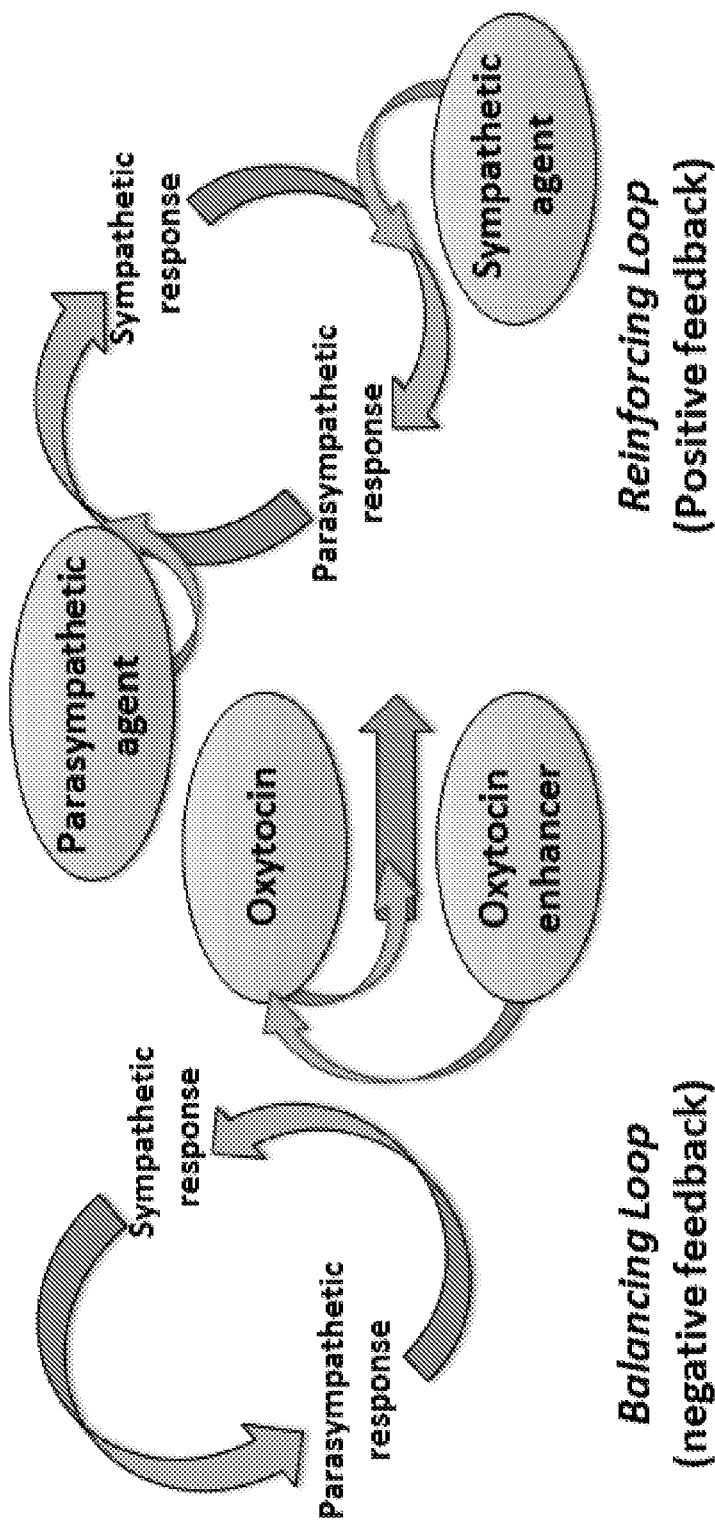
FIG. 3 presents a proposed model for interaction of sympathetic and parasympathetic systems in accordance with the present disclosure. In this proposed model B, oxytocin acts as the unknown variable and participates in transforming the mode of interaction between the sympathetic and parasympathetic arms of the autonomic nervous system from balancing to reinforcing. As the orchestrator of this transition, oxytocin modulates the biological context allowing other agents (that target either the parasympathetic or sympathetic systems) to enhance the sexual response. A combination agent could act as an oxytocin enhancer and help drive the transition and/or help drive the reinforcing loop. As in previous Figures, the loop to the left of the middle arrow depicts homeostatic conditions. The circular arrows pointing in the counterclockwise direction denote the regulatory, balancing interaction between the two arms of the autonomic nervous system. The loop to the right of central arrow, with the circular arrows pointing in the clockwise direction, symbolize the reinforcing interaction that oxytocin has helped promote. The oxytocin mediated transition would then allow the addition of parasympathetic and/or sympathetic enhancing agents, that would normally counteract each other, to help drive the reinforcing cycle of positive feedback, facilitating the sexual response. Similar to the previous model, oxytocin could both provide the context for other agents to enhance the sexual response and contribute as a driving agent by participating as a parasympathetic agent.
Figure 4:
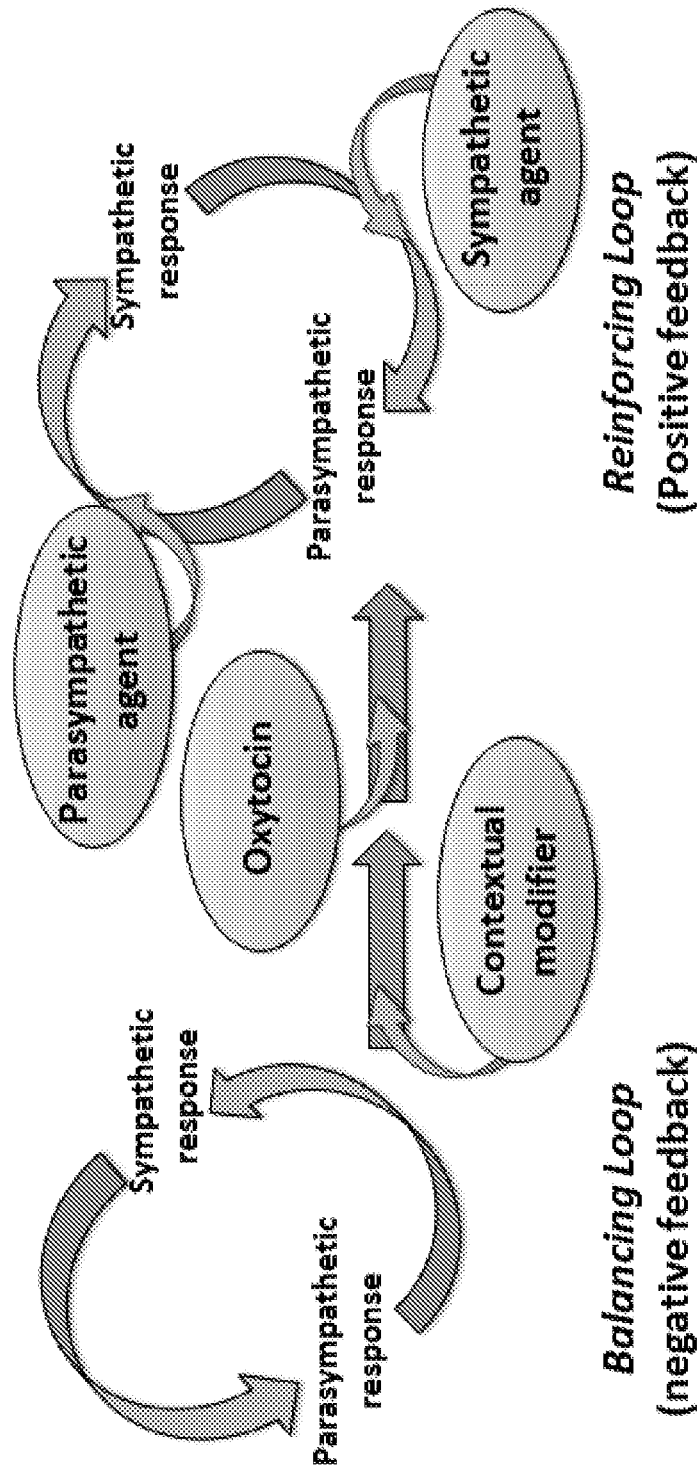
FIG. 4 presents a proposed model for interaction of sympathetic and parasympathetic systems in accordance with the present disclosure. This proposed model C involves agents (e.g., as described herein) acting as contextual modifiers, allowing the addition of oxytocin to promote the switch in the interaction between the sympathetic and parasympathetic arms of the autonomic nervous system from a regulatory, balancing mode to a positive, reinforcing, feedback mode. After the switch to a reinforcing mode, oxytocin may continue to enhance the circuit by driving the parasympathetic response. Additional parasympathetic and/or sympathetic agents could also contribute by now driving the reinforcing loop.

Without wishing to be bound by any particular theory or exemplification, the present disclosure provides proposed models A, B, and C (FIGS. 2, 3, and 4), each of which depicts combining oxytocin with another agent (an Oxytocin Enhancing Agent) to either promote or enhance the reinforcing, positive feedback between the parasympathetic and sympathetic arms of the autonomic nervous system necessary for successful sexual function.

As demonstrated over the many years of experimentation with the oxytocin peptide, exogenous administration of oxytocin produces inconsistent, often unexpected (Nishimori, Young et al. 1996, Bartz, Simeon et al. 2011), and sometimes controversial effects (De Dreu, Shalvi et al. 2012, Sheng, Liu et al. 2013). Without wishing to be bound by any particular theory, the present disclosure proposes that this uniquely complex pattern most likely largely rests on the fact that oxytocin's actions differ depending on the physiological and social context. The hormonal milieu, the relative balance between the parasympathetic and sympathetic autonomic nervous systems, and the proximity of other neuropeptides, neurotransmitters, magnesium, and cholesterol can all alter the activity of oxytocin and the downstream consequence of this peptide.

The present disclosure appreciates that such complexity may have discouraged development of oxytocin as a therapeutic agent. The present disclosure appreciates, however, that such context sensitivity, and the complexity of the oxytocin response, provides an opportunity to manipulate the environment through pharmacological means and to combine medications that in a different context would appear to oppose one another, to produce a reliably stimulatory effect on the human sexual response. Thus, this present disclosure proposes combining oxytocin with certain other medications (listed herein) to enhance both the sympathetic and parasympathetic response, necessary for a successful sexual response, by engaging oxytocin's ability to allow such simultaneous stimulation. In some embodiments, medications selected for use in combination with oxytocin, described herein, can modulate the context by priming the hormonal milieu, can activate both the sympathetic and/or parasympathetic pathways, or can augment the effect of oxytocin by altering the levels of neuropeptides and neurotransmitters that work in concert with oxytocin.

To date, in the human literature, no study has attempted to adjust the physiological context concomitant with, prior to, or directly after the administration of oxytocin, nor have other medications that target sexual dysfunction attempted to activate both the parasympathetic and sympathetic arms of the autonomic nervous system simultaneously. Several investigators, however, have attempted to administer oxytocin under differing psychological or social contexts, with the assumption that as a prosocial hormone, oxytocin may have varying effects given different social or psychological situations. In one study, investigators adjusted the financial vulnerability of the male subjects in an economics game to evaluate the effect of oxytocin on their generosity and inferred that oxytocin increased the subjects' tendency to protect weaker members of the group (De Dreu, Shalvi et al. 2012). In a separate study, investigators reported that oxytocin altered the subjective experience of light touch depending on whether heterosexual male subjects believed either a male or a female investigator applied the stimulus (Scheele, Kendrick et al. 2014). In a third study (Behnia, Heinrichs et al. 2014), the effect of exogenous oxytocin on biological sexual parameters was evaluated in a naturalistic setting between couples after the investigators had failed to find a beneficial effect of oxytocin on physical measures of the sexual response in the laboratory setting (Burri, Heinrichs et al. 2008). The change of social context from a laboratory setting to a more naturalistic setting with an established partner did not change oxytocin's effect on biological measures of sexual functioning. The couples reported improved subjective experiences, but none of the physiological measures of sexual functioning improved with this context manipulation. At no point in the discussions of these reports did the authors mention the possibility of altering context by adjusting physiological parameters through pharmacological manipulation.

In contrast to human studies, animal investigations of oxytocin often adjust the hormonal milieu prior to administration of oxytocin by either preloading the animals with steroid hormones (Kennett and McKee 2012) or castrating them (Tribollet, Audigier et al. 1990). The authors implemented these manipulations not to augment oxytocin's actions on the sexual response, but to control for confounding hormonal effects or to establish a specific hormonal profile such as pregnancy. One study, reported in 1996, determined that pretreatment of mice with estrogen enhanced the effect of oxytocin on animal measures of anxiety (McCarthy, McDonald et al. 1996). The investigators administered estrogen only to previously ovariectomized mice devoid of endogenous estrogen. They did not employ pretreatment with estrogen to wild type mice. Inferences about a synergistic effect of oxytocin and pretreatment with estrogen in circumstances other than ovariectomization cannot be made from this study. Ovariectomizing or castrating animals to control for steroid hormone production, injections of steroid hormones to mimic a developmental stage such as pregnancy, or administering hormone antagonists prior to oxytocin have all been implemented in animal studies with the aim to control for confounding factors, not to investigate potentially synergistic combinations of oxytocin with other medications to enhance its pro-sexual effect.

Reviews of the human sexual response acknowledge the importance of oxytocin and also detail oxytocin's interaction with other neurotransmitters in the brain. They do not discuss, however, how external adjustments in the pharmacologic milieu through medications or exogenous hormones may be harnessed to enhance the effect of oxytocin on the sexual response. Nor, conversely, does any author suggest using oxytocin as a context modifier to alter the efficacy of other sexual enhancement medications. No publication has ever mentioned how oxytocin may allow for simultaneous exogenous stimulation of both the parasympathetic and sympathetic arms of the autonomic nervous system to enhance sexual functioning. The present disclosure appreciates the context dependent nature of oxytocin's physiological activity, the ability of oxytocin to modulate the context or milieu to augment other medications, the unique ability of oxytocin to coordinate both arms of the autonomic nervous system, and how these characteristics may contribute to its usefulness in therapeutic regimens that expose subjects to oxytocin in combination with another agent as set forth herein.

Exemplary Oxytocin Enhancing Agents that may usefully be combined with oxytocin in accordance with teachings of the present disclosure include, for example (a-gg below):

Agents that mimic or enhance parasympathetic activity: Exemplary such agents may be selected from, for example, one or more of:

a. Cholinergic agonists (e.g., nicotine, alpha-7 agonists, varinecline, carbachol); such agents may mimic endogenous acetylcholine, the main transmitter of the parasympathetic nervous system.

b. Acetylcholine esterase inhibitors (e.g., Donepezil, Aricept®; Tacrine, Cognex®); such agents may increase the parasympathetic response by decreasing the degradation of acetylcholine, the primary neurotransmitter of the parasympathetic nervous system.

c. Alpha-2 adrenoreceptor antagonists (e.g., Yohimbine, phentolamine); such agents may indirectly enhance the parasympathetic response.

d. Nitric oxide activators (e.g., phosphodiesterase inhibitors, L-arginine); such agents can increase cGMP, a second messenger that transduces the parasympathetic signal.

e. Cholecystokinin (CCK) and/or its analogues; CCK participates in the transduction of the parasympathetic response.

f. Histaminergic agents (e.g., carnosine, betazole); such agents can elevate histamine, a secondary neurotransmitter that participates in the parasympathetic response.

g. Histamine receptor subtype 3 (HR3) antagonists (e.g., ABT-239, Ciproxifan, Clobenpropit, Thioperamide, Cipralisant); such agents may augment the primary histaminergic response, (see f above).

h. Prostaglandins (e.g., synthetic PGE1, anandamides); such agents can mimic down stream effectors of the parasympathetic response.

i. Vasoactive intestinal peptide (VIP) analogues or enhancers (e.g., that may provide degradation inhibition by blocking neutral endopeptidase, NED, or soluble endopeptidase, SED, pathway); such agents can augment VIP, a neuropeptide mentioned above that participates in the parasympathetic response.

Agents that mimic or enhance sympathetic activity: Exemplary such agents may be selected from, for example, one or more of:

j. Sympathomimetic agents (e.g.,alpha-1 agonists,such as pseudoephedrine); such agents can mimic endogenous epinephrine and/or norepinephrine, the primary neurotransmitter involved in the sympathetic response.

k. Buproprion; this medication can increase norepinephrine levels in the synaptic cleft.

l. Dopaminergic agents (e.g., amphetamines and stimulants such as methylphenidate, apomorphine, ABT-724); such agents can indirectly stimulate the sympathetic response.

m. CCK antagonists (e.g., proglumide); such agents potentially increase the sympathetic response by indirectly inhibiting parasympathetic activity.

n. Mirtazapine (typically administered 15-45 mg qD); this antidepressant medication can increase norepinephrine.

o. Vasopressin analogues; such agents potentially augments the sympathetic response.

Agents that enhance oxytocin secretion or could act as contextual modifiers to augment oxytocin's biological activity (for review of the physiological processes involved in oxytocin secretion, see Brown et al, 2013 (Brown, Bains et al. 2013): Exemplary such agents may be selected from, for example, one or more of:

p. Steroid hormones (e.g., testosterone, estrogen, and progesterone).

q. Prostoglandins (PG-E1) (e.g., alprostadil, synthetic analogue, typically prescribed in a topical formulation 400-900 ug).

r. Buspirone (5-HT1A partial agonist).

s. Travivo (5-HT1A agonist).

t. OPC-14523 (5-HT1A agonist).

u. Adrenocorticoptropin (ACTH).

v. Glutamatergic agents (e.g., choline, glycine, and d-cyclosporin).

w. Vitamin D and magnesium (such agents can augment oxytocin receptor sensitivity).

x. Cortisol reducers or glucocorticoid receptor antagonists (e.g., Ketaconozole).

y. Vitamin C (this vitamin enhances synthesis of oxytocin).

z. Aminopeptidase inhibitors (e.g., amastatin, bestatin (ubenimex), leupeptin, and puromycin; luepeptin is water soluble and can be given topically for middle ear infections); such agents can increase oxytocin levels, for example by preventing degradation.

aa. Oxytocin (for example, Syntocinon®, which is prescribed as 10 IU per dose, 2 doses in each nostril pm).

bb. CD38 enhancers (such agents can increase oxytocin release from the nerve terminals) (Salmina, Lopatina et al. 2010).

cc. Arginine (semi-essential amino acid that may increase oxytocin release via its potential ability to stimulate growth hormone).

Contextual modifiers or agents with known partial or inconsistent sexual enhancement capabilities. Exemplary such agents may be selected from, for example, one or more of:

dd. Melanocortins (a-melanocyte stimulating hormone receptor agonists (Pfaus, Giuliano et al. 2007), such as bremelanotide, which is typically dosed at: 50-200 micrograms/kg)

ee. Prolactin inhibitors (Kruger, Haake et al. 2003)

ff. Vasopressin gg. Flibanserin (5-HT1A agonist; 5-HT2A antagonist)

Administration

The present disclosure provides combination therapy regimens that expose a subject substantially simultaneously to a combination of oxytocin and at least one other agent as described herein. In some embodiments, oxytocin is administered to a subject who is receiving therapy with the other agent. In some embodiments, the other agent is administered to a subject who is receiving therapy with oxytocin. In some embodiments, therapy with both agents is initiated substantially simultaneously.

In some embodiments, oxytocin is administered intranasally, sublingually, and/or topically; in some embodiments, the other agent is administered intranasally, sublingually, and/or topically. In some embodiments, both agents are administered together in a single composition for at least one or more doses; in some embodiments the present disclosure provides unit dosage forms of pharmaceutical compositions that comprise oxytocin and at least one additional therapeutic agent as described herein.

In some embodiments, a topically applied contextual modifier, oxytocin enhancer, sympathomimetic, or parasympathomimetic agent would be given prior to or along with intranasal, sublingual or intrabuccal oxytocin. Examples of such combinations would be a topical application as a patch or a gel of progesterone or testosterone either ongoing or on a once daily dosing, such as a weekend morning, and then intranasal oxytocin (e.g., 20-40 international units, IU) 30-60 minutes prior to sexual engagement.

In other embodiments, an oral, intranasal, sublingual, or intrabuccal contextual modifier, oxytocin enhancer, sympathomimetic, or parasympathomimetic agent would be given along with, prior to, or after the administration of intranasal, sublingual, or intrabuccal oxytocin. In some embodiments, sublingual buspirone (e.g., 5-15 mg) would be administered in combination with intranasal oxytocin (e.g., 10-40 IU) prior to sexual engagement. In some embodiments, intranasal oxytocin (e.g., 10 to 40 IUs) would be administered along with or prior to a sympathomimetic agent such as intranasal (e.g., 0.5 to 1.0% solution) pseudoephedrine.

In other embodiments, oxytocin could be given as a topical agent to the genital area in the form of a lubricant, along with an oral, intranasal, sublingual, or intrabuccal form of a context modifier, oxytocin enhancer, sympathomimetic, or parasympathomimetic agent. An example of such an embodiment would include oral or sublingual buprorion (e.g., 50-150 mg) 2 hours to 30 minutes prior to engagement and then the addition of topical oxytocin lubricant (1% solution) just prior to initiation of activity.

In some embodiments, a contextual modifier (topical, oral, intranasal, or sublingual) would be given prior to or along with oxytocin (intranasal, sublingual, topical, or intrabuccal) in combination with another driving agent, such as a sympathomimetic medication. An example of such an embodiment would be the administration of buspirone (e.g., 5-15 mg sublingual) in combination with intranasal oxytocin (e.g., 10-40 IUs), followed by a topical or formulation of pseudoephedrine (e.g., 1% solution) as a genitally applied lubricant.

EXEMPLIFICATION

Example 1

Over four separate occasions, a patient sequentially self-administered Syntocinon® nasal spray (40 IU) and 0.5% Neo-Synephrine® nasal spray (Phenylephrine hydrochloride) 5 to 20 min prior to sexual activity. Upon completion of sexual activity, the patient self-reported the outcome of the qualities associated with the sexual experience based on the following criteria:
1. Ease of orgasm (0-5 scale, where 0=no orgasm and 5=easiest ever experienced)
2. Strength of orgasm (0-5 scale, where 0=no orgasm and 5=strongest contractions ever experienced)
3. Desire (0-5 scale, where 0=no interest and 5=self-initiated and more intense than ever experienced)
4. Arousal (0-5 scale, where 0=no lubrication or heightened sensitivity and 5=most extreme arousal ever experienced)

The results of four trials are summarized below:
1. Ease of orgasm (baseline=2)
    Range: 3-5
    Mean: of 3.5
2. Strength of orgasm (baseline=2-3)
    Range: 3-5
    Mean: 3.75
3. Desire (baseline=2-3)
    Range: Unchanged from baseline
    Mean: Unchanged from baseline
4. Arousal (baseline=2-3)
    Range: 2-5
    Mean: 3.25

REFERENCES

Anderson-Hunt, M. and L. Dennerstein (1994). "Increased female sexual response after oxytocin." *BMJ* 309(6959): 929.

Argiolas, A. and M. R. Melis (2004). "The role of oxytocin and the paraventricular nucleus in the sexual behaviour of male mammals." *Physiol Behav* 83(2): 309-317.

Argiolas, A. and M. R. Melis (2013). "Neuropeptides and central control of sexual behaviour from the past to the present: A review." *Prog Neurobiol.*

Bales, K. L. and C. S. Carter (2003). "Developmental exposure to oxytocin facilitates partner preferences in male prairie voles (Microtus ochrogaster)." *Behav Neurosci* 117 (4): 854-859.

Bartz, J., D. Simeon, H. Hamilton, S. Kim, S. Crystal, A. Braun, V. Vicens and E. Hollander (2011). "Oxytocin can hinder trust and cooperation in borderline personality disorder." *Social Cognitive and Affective Neuroscience* 6(5): 556-563.

Baskerville, T. A. and A. J. Douglas (2008). "Interactions between dopamine and oxytocin in the control of sexual behaviour." *Prog Brain Res* 170: 277-290.

Baumgartner, T., M. Heinrichs, A. Vonlanthen, U. Fischbacher and E. Fehr (2008). "Oxytocin shapes the neural circuitry of trust and trust adaptation in humans." *Neuron* 58: 639-650.

Behnia, B., M. Heinrichs, W. Bergmann, S. Jung, J. Germann, M. Schedlowski, U. Hartmann and T. H. Kruger (2014). "Differential effects of intranasal oxytocin on sexual experiences and partner interactions in couples." *Horm Behav* 65(3): 308-318.

Boyd, N. R. (1972). "Oxytocin in human parturition." *Proc R Soc Med* 65(5): 491-492.

Brown, C. H., J. S. Bains, M. Ludwig and J. E. Stern (2013). "Physiological regulation of magnocellular neurosecretory cell activity: integration of intrinsic, local and afferent mechanisms." *J Neuroendocrinol* 25(8): 678-710.

Burri, A., M. Heinrichs, M. Schedlowski and T. H. Kruger (2008). "The acute effects of intranasal oxytocin administration on endocrine and sexual function in males." *Psychoneuroendocrinology* 33(5): 591-600.

Cara, A. M., R. A. Lopes-Martins, E. Antunes, C. R. Nahoum and G. De Nucci (1995). "The role of histamine in human penile erection." *Br J Urol* 75(2): 220-224.

Carmichael, M. S., R. Humbert, J. Dixen, G. Palmisano, W. Greenleaf and J. M. Davidson (1987). "Plasma oxytocin increases in the human sexual response." *J Clin Endocrinol Metab* 64(1): 27-31.

Carmichael, M. S., V. L. Warburton, J. Dixen and J. M. Davidson (1994). "Relationships among cardiovascular, muscular, and oxytocin responses during human sexual activity." *Arch Sex Behav* 23(1): 59-79.

De Dreu, C. K. W., S. Shalvi, L. L. Greer, G. A. Van Kleef and M. J. J. Handgraaf (2012). "Oxytocin Motivates Non-Cooperation in Intergroup Conflict to Protect Vulnerable In-Group Members." *PLoS One* 7(11): e46751.

de Jong, T. R. and I. D. Neumann (2015). "Moderate Role of Oxytocin in the Pro-Ejaculatory Effect of the 5-HT1A Receptor Agonist 8-OH-DPAT." *J Sex Med* 12(1): 17-28.

Dinsmore, W. W. and M. G. Wyllie (2008). "Vasoactive intestinal polypeptide/phentolamine for intracavernosal injection in erectile dysfunction." *BJU Int* 102(8): 933-937.

Feifel, D. (2012). "Oxytocin as a potential therapeutic target for schizophrenia and other neuropsychiatric conditions." Neuropsychopharmacology 37(1): 304-305.

Feifel, D., K. Macdonald, P. Cobb and A. Minassian (2012). "Adjunctive intranasal oxytocin improves verbal memory in people with schizophrenia." *Schizophr Res* 139 (1-3): 207-210.

Feifel, D., K. Macdonald, A. Nguyen, P. Cobb, H. Warlan, B. Galangue, A. Minassian, O. Becker, J. Cooper, W. Perry, M. Lefebvre, J. Gonzales and A. Hadley (2010). "Adjunctive intranasal oxytocin reduces symptoms in schizophrenia patients." *Biol Psychiatry* 68: 678-680.

Feifel, D. and T. Reza (1999). "Oxytocin modulates psychotomimetic-induced deficits in sensorimotor gating." *Psychopharmacology* 141: 93-98.

Feifel, D., P. D. Shilling and A. M. Belcher (2012). "The effects of oxytocin and its analog, carbetocin, on genetic deficits in sensorimotor gating." *Eur Neuropsychopharmacol* 22(5): 374-378.

Fuchs, A. R. and F. Fuchs (1984). "Endocrinology of human parturition: a review." *Br J Obstet Gynaecol* 91(10): 948-967.

Giraldi, A., A. S. Enevoldsen and G. Wagner (1990). "Oxytocin and the initiation of parturition. A review." *Dan Med Bull* 37(4): 377-383.

Haeger, K. and D. Jacobsohn (1953). "A contribution to the study of milk ejection in women." *Acta Physiol Scand Suppl* 111: 152-160.

Hatton, G. I. and Y. F. Wang (2008). "Neural mechanisms underlying the milk ejection burst and reflex." *Prog Brain Res* 170: 155-166.

Heil, S. H. and M. G. Subramanian (1998). "Alcohol and the hormonal control of lactation." *Alcohol Health Res World* 22(3): 178-184.

Insel, T. R. (1990). "Regional changes in brain oxytocin receptors post-partum: time-course and relationship to maternal behaviour." *J Neuroendocrinol* 2(4): 539-545.

Insel, T. R. and L. E. Shapiro (1992). "Oxytocin receptors and maternal behavior." *Ann N Y Acad Sci* 652: 122-141.

Insel, T. R., J. T. Winslow, Z. X. Wang, L. Young and T. J. Hulihan (1995). "Oxytocin and the molecular basis of monogamy." *Adv Exp Med Biol* 395: 227-234.

Insel, T. R., L. Young and Z. Wang (1997). "Molecular aspects of monogamy." *Ann N Y Acad Sci* 807: 302-316.

Ishak, W. W., D. S. Berman and A. Peters (2008). "Male anorgasmia treated with oxytocin." *J Sex Med* 5(4): 1022-1024.

Jing, J., F. S. Vilim, C. C. Horn, V. Alexeeva, N. G. Hatcher, K. Sasaki, I. Yashina, Y. Zhurov, I. Kupfermann, J. V. Sweedler and K. R. Weiss (2007). "From Hunger to Satiety: Reconfiguration of a Feeding Network by Aplysia Neuropeptide Y." *The Journal of Neuroscience* 27(13): 3490-3502.

Kennett, J. E. and D. T. McKee (2012). "Oxytocin: an emerging regulator of prolactin secretion in the female rat." *J Neuroendocrinol* 24(3): 403-412.

Keri, S. and I. Kiss (2011). "Oxytocin response in a trust game and habituation of arousal." *Physiol Behav* 102(2): 221-224.

Kosfeld, M., M. Heinrichs, P. Zak, U. Fischbacher and E. Fehr (2005). "Oxytocin increases trust in humans." *Nature* 435: 673-676.

Kruger, T. H., P. Haake, D. Chereath, W. Knapp, O. E. Janssen, M. S. Exton, M. Schedlowski and U. Hartmann (2003). "Specificity of the neuroendocrine response to orgasm during sexual arousal in men." *J Endocrinol* 177(1): 57-64.

Kruger, T. H., B. Schiffer, M. Eikermann, P. Haake, E. Gizewski and M. Schedlowski (2006). "Serial neurochemical measurement of cerebrospinal fluid during the human sexual response cycle." *Eur J Neurosci* 24(12): 3445-3452.

Lazzari, V. M., R. O. Becker, M. S. de Azevedo, M. Morris, K. Rigatto, S. Almeida, A. B. Lucion and M. Giovenardi (2013). "Oxytocin modulates social interaction but is not essential for sexual behavior in male mice." *Behav Brain Res* 244: 130-136.

Lidberg, L. and V. Sternthal (1977). "A new approach to the hormonal treatment of impotentia erections." *Pharmakopsychiatr Neuropsychopharmakol* 10(1): 21-25.

MacDonald, K. (2009). "Patient-clinician eye contact: social neuroscience and art of clinical engagement." *Postgrad Med* 121(4): 136-144.

MacDonald, K. and D. Feifel (2012). "Dramatic improvement in sexual function induced by intranasal oxytocin." *J Sex Med* 9(5): 1407-1410.

Macdonald, K. and D. Feifel (2012). "Oxytocin in schizophrenia: a review of evidence for its therapeutic effects." *Acta Neuropsychiatr* 24(3): 130-146.

Macdonald, K. and D. Feifel (2013). "Helping oxytocin deliver: considerations in the development of oxytocin-based therapeutics for brain disorders." *Front Neurosci* 7:35.

Macdonald, K. and T. M. Macdonald (2010). "The peptide that binds: a systematic review of oxytocin and its prosocial effects in humans." *Harv Rev Psychiatry* 18(1): 1-21.

Macdonald, K. S. (2012). "Sex, receptors, and attachment: a review of individual factors influencing response to oxytocin." *Front Neurosci* 6: 194.

McCarthy, M. M., C. H. McDonald, P. J. Brooks and D. Goldman (1996). "An anxiolytic action of oxytocin is enhanced by estrogen in the mouse." *Physiol. Behav.* 60: 1209-1215.

Montgomery, S. A., D. S. Baldwin and A. Riley (2002). "Antidepressant medications: a review of the evidence for drug-induced sexual dysfunction." *Journal of Affective Disorders* 69(1-3): 119-140.

Murphy, M. R., J. R. Seckl, S. Burton, S. A. Checkley and S. L. Lightman (1987). "Changes in oxytocin and vasopressin secretion during sexual activity in men." *J Clin Endocrinol Metab* 65(4): 738-741.

Nishimori, K., L. J. Young, Q. Guo, Z. Wang, T. R. Insel and M. M. Matzuk (1996). "Oxytocin is required for nursing but is not essential for parturition or reproductive behavior." *Proc Natl Acad Sci USA* 93(21): 11699-11704.

Ogawa, S., S. Kudo, Y. Kitsunai and S. Fukuchi (1980). "Increase in oxytocin secretion at ejaculation in male." *Clin Endocrinol* (Oxf) 13(1): 95-97.

Pfaus, J., F. Giuliano and H. Gelez (2007). "Bremelanotide: an overview of preclinical CNS effects on female sexual function." *J Sex Med* 4 Suppl 4: 269-279.

Renfrew, M. J., S. Lang and M. Woolridge (2000). "Oxytocin for promoting successful lactation." *Cochrane Database Syst Rev*(2): CD000156.

Salmina, A. B., O. Lopatina, M. V. Ekimova, S. V. Mikhutkina and H. Higashida (2010). "CD38/cyclic ADP-ribose system: a new player for oxytocin secretion and regulation of social behaviour." *J Neuroendocrinol* 22(5): 380-392.

Scheele, D., K. M. Kendrick, C. Khouri, E. Kretzer, T. E. Schlapfer, B. Stoffel-Wagner, O. Gunturkun, W. Maier and R. Hurlemann (2014). "An oxytocin-induced facilitation of neural and emotional responses to social touch correlates inversely with autism traits." *Neuropsychopharmacology* 39(9): 2078-2085.

Shapiro, L. E. and T. R. Insel (1992). "Oxytocin receptor distribution reflects social organization in monogamous and polygamous voles." *Ann N Y Acad Sci* 652: 448-451.

Sheng, F., Y. Liu, B. Zhou, W. Zhou and S. Han (2013). "Oxytocin modulates the racial bias in neural responses to others' suffering." *Biol Psychol* 92(2): 380-386.

Tribollet, E., S. Audigier, M. Dubois-Dauphin and J. J. Dreifuss (1990). "Gonadal steroids regulate oxytocin receptors but not vasopressin receptors in the brain of male and female rats. An autoradiographical study." *Brain Research* 511(1): 129-140.

Walch, K., R. Eder, A. Schindler and W. Feichtinger (2001). "The effect of single-dose oxytocin application on time to ejaculation and seminal parameters in men." *J Assist Reprod Genet* 18(12): 655-659.

Williams, J. R., T. R. Insel, C. R. Harbaugh and C. S. Carter (1994). "Oxytocin administered centrally facilitates formation of a partner preference in female prairie voles (Microtus ochrogaster)." *J Neuroendocrinol* 6(3): 247-250.

Young, L. J., A. Z. Murphy Young and E. A. Hammock (2005). "Anatomy and neurochemistry of the pair bond." *J Comp Neurol* 493(1): 51-57.

Young, L. J., Z. Wang and T. R. Insel (1998). "Neuroendocrine bases of monogamy." *Trends Neurosci* 21(2): 71-75.

EQUIVALENTS

Those skilled in the art will recognize, or be able to ascertain using no more than routine experimentation, many equivalents to the specific embodiments of the invention described herein. The scope of the present invention is not intended to be limited to the above Description, but rather is as set forth in the following claims:

The invention claimed is:

1. A method comprising administering to a subject suffering from sexual dysfunction intranasal oxytocin, wherein the subject has received or is receiving at least one sublingual 5-HT1A partial agonist, so that the subject receives combination therapy with both.

2. The method of claim 1, wherein the step of administering comprises administering both the intranasal oxytocin and the sublingual 5-HT1A partial agonist to the subject.

3. The method of claim 1, wherein the sexual dysfunction is (i) delayed orgasm and/or (ii) difficulty achieving orgasm and is secondary to current and/or prior use of psychotropic medications.

4. The method of claim 1, wherein the subject is a woman.

5. The method of claim 4, wherein the subject is a post-menopausal woman.

6. The method of claim 1, wherein the subject does not adequately respond to available medications or is unable to tolerate available medications because of side effects and/or contraindications.

7. The method of claim 1, wherein the subject is a male.

8. The method of claim 1, wherein the step of administering the intranasal oxytocin occurs approximately 5 minutes to six hours prior to sexual activity.

9. The method of claim 8, wherein the step of administering the intranasal oxytocin occurs approximately 30 minutes to 120 minutes, 30 minutes to 60 minutes, or 5 minutes to 20 minutes prior to sexual activity.

10. The method of claim 1, further comprising administration of at least one additional agent that (i) modulates one or more of parasympathetic activity, sympathetic activity, or oxytocin secretion and/or (ii) can act as a contextual modifier to augment biological activity of oxytocin.

11. The method of claim 1, wherein the intranasal oxytocin is administered prior to the at least one sublingual 5-HT1A partial agonist.

12. The method of claim 10, wherein the at least one additional agent is administered prior to, subsequent to, or concomitant with (i) the intranasal oxytocin; and/or (ii) the at least one sublingual 5-HT1A partial agonist.

13. A method comprising administering to a subject suffering from sexual dysfunction at least one sublingual 5-HT1A partial agonist, wherein the subject has received or is receiving intranasal oxytocin, so that the subject receives combination therapy with both.

14. The method of claim 13, wherein the step of administering comprises administering both the at least one sublingual 5-HT1A partial agonist and the intranasal oxytocin to the subject.

15. The method of claim 13, wherein the sexual dysfunction is (i) delayed orgasm and/or (ii) difficulty achieving orgasm and is secondary to current and/or prior use of psychotropic medications.

16. The method of claim 13, wherein the subject is a woman.

17. The method of claim 13, wherein the subject is a post-menopausal woman.

18. The method of claim 13, wherein the subject does not adequately respond to available medications or is unable to tolerate available medications because of side effects and/or contraindications.

19. The method of claim 13, wherein the subject is a male.

20. The method of claim 13, wherein the step of administering the at least one sublingual 5-HT1A partial agonist occurs approximately 5 minutes to six hours prior to sexual activity.

21. The method of claim 20, wherein the step of administering the at least one sublingual 5-HT1A partial agonist occurs approximately 30 minutes to 120 minutes, 30 minutes to 60 minutes, or 5 minutes to 20 minutes prior to sexual activity.

22. The method of claim 13, further comprising administration of at least one additional agent that (i) modulates one or more of parasympathetic activity, sympathetic activity, or oxytocin secretion and/or (ii) can act as a contextual modifier to augment biological activity of oxytocin.

23. The method of claim 13, wherein the at least one sublingual 5-HT1A partial agonist is administered concomitant with the intranasal oxytocin.

24. The method of claim 13, wherein the at least one sublingual 5-HT1A partial agonist is administered prior to the intranasal oxytocin.

25. The method of claim 22, wherein the at least one additional agent is administered prior to, subsequent to, or concomitant with (i) the at least one sublingual 5-HT1A partial agonist and/or (ii) the intranasal oxytocin.

* * * * *